(12) United States Patent
Buelow

(10) Patent No.: US 9,388,233 B2
(45) Date of Patent: *Jul. 12, 2016

(54) RAT HAVING A DISRUPTED IMMUNOGLOBULIN GENE

(76) Inventor: Roland Buelow, Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/192,407

(22) Filed: Jul. 27, 2011

(65) Prior Publication Data

US 2012/0090041 A1 Apr. 12, 2012

Related U.S. Application Data

(62) Division of application No. 12/130,818, filed on May 30, 2008, now Pat. No. 8,703,485.

(60) Provisional application No. 61/044,324, filed on Apr. 11, 2008, provisional application No. 60/941,619, filed on Jun. 1, 2007.

(51) Int. Cl.
*A01K 67/00* (2006.01)
*C07K 16/00* (2006.01)
*A01K 67/027* (2006.01)
*C12N 15/85* (2006.01)
*C12N 9/22* (2006.01)

(52) U.S. Cl.
CPC ............. *C07K 16/00* (2013.01); *A01K 67/0278* (2013.01); *C12N 9/22* (2013.01); *C12N 15/8509* (2013.01); *A01K 2217/072* (2013.01); *A01K 2267/01* (2013.01)

(58) Field of Classification Search
USPC .................................................. 800/14, 8, 18
See application file for complete search history.

(56) References Cited

U.S. PATENT DOCUMENTS

| | | | |
|---|---|---|---|
| 5,574,205 A * | 11/1996 | Kucherlapati et al. ............. 800/3 |
| 5,721,367 A | 2/1998 | Kay et al. |
| 5,939,598 A * | 8/1999 | Kucherlapati et al. .......... 800/25 |
| 6,075,181 A * | 6/2000 | Kucherlapati et al. .......... 800/25 |
| 6,114,598 A * | 9/2000 | Kucherlapati et al. .......... 800/18 |
| 6,139,835 A * | 10/2000 | Kucherlapati et al. ..... 424/93.21 |
| 6,150,584 A * | 11/2000 | Kucherlapati et al. .......... 800/18 |
| 6,162,963 A * | 12/2000 | Kucherlapati et al. .......... 800/18 |
| 6,514,752 B1 * | 2/2003 | Kucherlapati et al. ..... 435/320.1 |
| 6,528,313 B1 | 3/2003 | Le Mouellic |
| 6,528,314 B1 | 3/2003 | Le Mouellic |
| 6,586,251 B2 | 7/2003 | Economides et al. |
| 6,596,541 B2 | 7/2003 | Murphy et al. |
| 6,657,103 B1 * | 12/2003 | Kucherlapati et al. ............. 800/6 |
| 6,673,986 B1 * | 1/2004 | Kucherlapati et al. .......... 800/18 |
| 6,713,610 B1 * | 3/2004 | Kucherlapati et al. ... 530/388.23 |
| 7,064,244 B2 * | 6/2006 | Jakobovits et al. ............. 800/18 |
| 7,098,031 B2 | 8/2006 | Choulika et al. |
| 7,129,084 B2 * | 10/2006 | Buelow et al. ............. 435/320.1 |
| 7,491,866 B2 | 2/2009 | Hammer et al. |
| 7,585,668 B2 * | 9/2009 | Buelow et al. ............. 435/320.1 |
| 8,137,966 B2 | 3/2012 | Teratani et al. |
| 8,502,018 B2 | 8/2013 | Murphy et al. |
| 8,652,842 B2 | 2/2014 | Platzer et al. |
| 2003/0017534 A1 * | 1/2003 | Buelow et al. ............... 435/69.1 |
| 2004/0158880 A1 * | 8/2004 | Buelow et al. .................... 800/6 |
| 2004/0199934 A1 | 10/2004 | Hess et al. |
| 2005/0064474 A1 | 3/2005 | Urnov |
| 2005/0153392 A1 * | 7/2005 | Buelow et al. ............... 435/69.1 |
| 2005/0229263 A1 * | 10/2005 | Buelow ............................. 800/8 |
| 2006/0026696 A1 * | 2/2006 | Buelow et al. .................... 800/6 |
| 2006/0026703 A1 * | 2/2006 | Lonberg et al. ................. 800/18 |
| 2006/0117398 A1 * | 6/2006 | Buelow et al. .................. 800/14 |
| 2006/0153826 A1 * | 7/2006 | Arnould et al. ............ 424/94.61 |
| 2006/0206949 A1 * | 9/2006 | Arnould et al. ................. 800/14 |
| 2008/0209587 A1 * | 8/2008 | Liljedahl et al. .............. 800/278 |

FOREIGN PATENT DOCUMENTS

| | | |
|---|---|---|
| EP | 1854473 A | 11/2007 |
| WO | WO 98/24893 A2 | 11/1998 |
| WO | WO 02/12437 A2 | 2/2002 |
| WO | WO 03047336 A2 | 6/2003 |
| WO | WO 2004/067736 A2 | 8/2004 |
| WO | WO 2005/014650 A2 | 2/2005 |
| WO | WO 2005/038001 A2 | 4/2005 |

OTHER PUBLICATIONS

Porteus (Nature Biotech, Aug. 2005, vol. 23, No. 8, p. 967-973).*
Donoho (Mol. Cell. Biol., Jul. 1998, vol. 18, No. 7, p. 4070-4078).*
Vasquez (PNAS, Jul. 17, 2001, vol. 98, No. 15, p. 8403-8410).*
Pabo (Annual Rev. Biochem., 2001, vol. 70, p. 313-340).*
Geurts (Science, 2009, vol. 325, p. 433).*
Geurts (Science, 2009, vol. 325, p. 433, Supplement Online Materials.*
IgM heavy chain constant gene segment (Rat Genome Database ID: 1359202) 2005.*
IgG heavy chain 2a gene segment (Rat Genome Database ID: 1359626) 2005.*
Isaiah (Methods in Enzymology, 2001, vol. 340, p. 593-609).*
Si-Hoe (Molecular Biotechnol., 2001, vol. 17, p. 151-182).*
Popova (Theriogenology, 2004, vol. 61, p. 1441-1453).*
Saunders (Transgenic Res., 2005, vol. 14, p. 483-529; abstract 18 on p. 494).*
Filipiak (Transgenic Res., 2006, vol. 15, p. 673-686).*
Buehr (Cell, Dec. 26, 2008, vol. 135, p. 1287-1298).*
Li (Cell, Dec. 26, 2008, vol. 135, No. 7, p. 1299-1310).*
Tong (Nature, Sep. 9, 2010, vol. 467, No. 7312, p. 211-213).*
Carbery (Genetics, Oct. 2010, vol. 186, p. 451-459).*
Cui (Nature Biotechnology, Jan. 2011, vol. 29, No. 1, p. 64-67).*
Hong (2012, Stem Cells and Development, vol. 21, No. 9, p. 1571-1586).*
Men (Stem Cells and Develop., Mar. 28, 2012, vol. 21, No. 14, p. 2606-2612).*
Gorman, S.D., "Reshaping a Therapeutic CD4 Antibody," Proc. Natl. Acad. Sci., 88(10):4181-4185 (1991).
Mendez, M.J., et al., "Functional Transplant of Megabase Human Immunoglobulin Loci Recapitulates Human Antibody Response in Mice," Nature Genetics, 15(2):146-156 (1997).

(Continued)

*Primary Examiner* — Michael Wilson
(74) *Attorney, Agent, or Firm* — Arnold & Porter LLP; Todd A. Lorenz

(57) ABSTRACT

The invention relates to transgenic animals lacking endogenous Ig and capable of producing transgenic antibodies, as well as methods of making the same. The invention further relates to methods for producing transgenic antibodies in such animals, and transgenic antibodies so produced.

5 Claims, 6 Drawing Sheets

(56) References Cited

OTHER PUBLICATIONS

Porteus, M.H., et al., "Gene Targeting Using Zinc Finger Nucleases," Nature Biotechnology, 23(8):967-973 (2005).
Smith, Julianne, et al., "A combinatorial approach to create artificial homing endonucleas es cleaving chosen sequences," Nucleic Acids Research, 34(22) (2006).
Zarrin, Ali A., et al., "Antibody class switching mediated by yeast endonuclease-generated DNA breaks," Science, 315(5810):377-381 (2007).
Guerts, Aron M., et al., "Knockout Rats via Embryo Microinjection of Zinc-Finger Nucleaes," Science, 325(5939):433 (2009).
Buelow, Roland et al., "Expression of a Humanized Antibody Repertoire in Transgenic Rabbits," Human Antibodies, 15(1-2):19-23 (2006).
Jakobovits, Aya, et al., "From XenoMouse technology to panitumumab, the first fully human antibody product from transgenic mice," Nature Biotechnology, 25(10):1134-1143 (2007).
Janssens, et al., "Generation of heavy-chain-only antibodies in mice", (2006) PNAS 103(41): 15130-15135.
Argast et al. "I-Ppol and I-Crel homing site sequence degeneracy determined by random mutagenesis and sequential in vitro enrichment." J. Mol. Biol. vol. 280, pp. 345-353 (1998).
Beumer, et al., "Efficient gene targeting in *Drosophila* by direct embryo injection with zinc-finger nucleases."PNAS vol. 105(50), pp. 19821-19826 (2008).
Biery et al., "Gene transfer by pronuclear injection in the bovine," Theriogenology 29(1):224-225 (1988).
Brem et al., Production of transgenic rabbits, mice and pigs by microinjection into pronuclei: Zuchthygiene, 20:251-252 (1985).
Bruggemann et al., "A repertoire of monoclonal antibodies with human heavy chains from transgenic mice." PNAS vol. 86, pp. 6709-6713 (1989).
Bruggemann et al., "Human Antibody Production in Transgenic Animals." Arch. Immunol. Ther. Exp. vol. 63, pp. 101-108 (2015).
Bruggemann et al., "Human antibody production in transgenic mice: expression from 100 kb of the human IgH locus." Eur. J. Immunol. vol. 21, pp. 1323-1326 (1991).
Bryda et al., "Method for detection and identification of multiple chromosomal integration sites in transgenic animals created with lentivirus." Biotechniques vol. 41(6), pp. 715-719 (2007).
Capecchi, "Altering the genome by homologous recombination." Science vol. 244(4910), pp. 1288-1292 (1989).
Chen and Zhao, "A highly sensitive selection method for directed evolution of homing endonucleases." Nucleic Acid Research vol. 33(18), pp. e154 (2005).
Choulika et al., "Induction of homologous recombination in mammalian chromosomes by using the I-ScelI system of *Saccharomyces cerevisiae*." Mol. Cell. Biol. vol. 15(4), pp. 1968-1973 (1995).
Cohen-Tannoudji et al., "I-*Scel*-induced gene replacement at a natural locus in embryonic stem cells." Mol. Cell. Biol. vol. 18(3), pp. 1444-1448 (1998).
Cronkhite et al., "Male and female germline specific expression of an EGFP reporter gene in a unique strain of transgenic rats." Dev. Biol. vol. 284(1), pp. 171-183 (2005).
Gordon et al, "Genetic transformation of mouse embryos by microinjection of purified DNA." PNAS vol. 77(12), pp. 7380-7384 (1980).
Hammer et al., "Production of transgenic mice, rabbits and pigs by microinjection." Nature vol. 315, pp. 680-683 (1985).
Hochi et al., "Successful production of transgenic rats." Animal Biotech. vol. 1, pp. 175-184 (1990).
Johnson et al., "Double-strand-break-induced homologous recombination in mammalian cells." Biochem. Soc. Trans. vol. 29(2), pp. 196-201 (2001).
Kitamura and Rajewky, "Targeted disruption of mu chain membrane exon causes loss of heavy-chain allelic exclusion." Nature vol. 356(6365), pp. 154-156 (1992).
Liu et al., "Regulation of an endogenous locus using a panel of designed zinc finger proteins targeted to accessible chromatin regions. Activation of vascular endothelial growth factor A." J. Biol. Chem. vol. 276(14), pp. 11323-11334 (2001).
MacPherson et al., "IgA production without μ or δ chain expression in developing B cells." Nature Immunol. vol. 2(7), pp. 625-631 (2001).
McConnel Smith et al., "Generation of a nicking enzyme that stimulates site-specific gene conversion from the I-AniI LAGLIDADG homing endonuclease." PNAS vol. 106(13), pp. 5099-5104 (2009).
Moehle et al., "Targeted gene addition into a specified location in the human genome using designed zinc finger nucleases." PNAS vol. 104(9), pp. 3055-3060 (2007).
Nguyen et al.."Heavy-chain only antibodies derived from dromedary are secreted and displayed by mouse B cells." Immunology vol. 109(1), pp. 93-101 (2003).
Ohbayashi et al., "Correction of chromosomal mutation and random integration in embryonic stem cells with helper-dependent adenoviral vectors." PNAS vol. 102(38), pp. 13628-13633 (2005).
Osborn et al., "High-Affinity IgG Antibodies Develop Naturally in Ig-Knockout Rats Carrying Germline Human IgH/Igk/IgλLci Bearing the Rat CH Region." J. Immunol. vol. 190, pp. 1481-1490 (2013).
Remy et al., "Efficient gene targeting by homology-directed repai in rat zygotes using TALE nucleases." Genome Res. vol. 24, pp. 1371-1383 (2014).
Ren et al., "Silencing of the immunoglobulin heavy chain locus by removal of all eight constant-region genes in a 200-kb region." Genomics vol. 84, pp. 686-695 (2004).
Rouet et al., "Introduction of double-strand breaks into the genome of mouse cells by expression of a rare-cutting endonuclease." Mol. Cell. Biol. vol. 14(12), pp. 8096-8106 (1994).
Townsend et al., "High-frequency modification of plant genes using engineered zinc-finger nucleases." Nature vol. 459(7245), pp. 442-445 (2009).
Van Keuren et al., "Generating transgenic mice from bacterial artificial chromosomes: transgenesis efficiency, integration and expression outcomes." Transgenic Res. vol. 18(5), pp. 769-785 (2009).
Wagner et al., "Microinjection of a rabbit β-globin gene into zygotes and its subsequent expression in adult mice and their offspring(gene transfer/interspecific gene expression)." PNAS vol. 78(10), pp. 6376-6380 (1981).
Wagner et al., "The human β-globin gene and functional viral thymidine kinase gene in developing mice." PNAS vol. 78(8), pp. 5016-5020 (1981).
Zou et al., "Block in development at the pre-B-1 1 to immature B cell stage in mice without Ig kappa and Ig lambda light chain." J. Immunol. vol. 170, pp. 1354-1361 (2003).
Zou et al., "Cre-loxP-Mediated Gene replacement: A Mouse Strain Producing Humanized Antibodies." Current Biology vol. 4, pp. 1099-1103 (1994).

* cited by examiner

Figure 2. Interaction of I-SceI and DNA at 3' end of recognition sequence

Figure 3. Interaction of the 5' end of the I-SceI recognition sequence with I-SceI.

Figure 4. Sequence recognition mechanism of I-CreI

Figure 5. Schematic diagram of the strategy for altering recognition sequence of I-CreI.

SEQUENCE LISTING

<160> NUMBER OF SEQ ID NOS: 58

<210> SEQ ID NO 1
<211> LENGTH: 18
<212> TYPE: DNA
<213> ORGANISM: Rattus rattus

<400> SEQUENCE: 1
cgtggatcac agggtct                    18

<210> SEQ ID NO 2
<211> LENGTH: 18
<212> TYPE: DNA
<213> ORGANISM: Rattus rattus

<400> SEQUENCE: 2
ctgggataac aggaagga                   18

<210> SEQ ID NO 3
<211> LENGTH: 18
<212> TYPE: DNA
<213> ORGANISM: Rattus rattus

<400> SEQUENCE: 3
tagggataac agggtaat                   18

<210> SEQ ID NO 4
<211> LENGTH: 18
<212> TYPE: DNA
<213> ORGANISM: Artificial Sequence
<220> FEATURE:
<223> OTHER INFORMATION: Synthetic

<400> SEQUENCE: 4
tagggataac agggtct                    18

<210> SEQ ID NO 5
<211> LENGTH: 18
<212> TYPE: DNA
<213> ORGANISM: Artificial Sequence
<220> FEATURE:
<223> OTHER INFORMATION: Synthetic

<400> SEQUENCE: 5
cgtggataac agggtct                    18

<210> SEQ ID NO 6
<211> LENGTH: 18
<212> TYPE: DNA
<213> ORGANISM: Artificial Sequence
<220> FEATURE:
<223> OTHER INFORMATION: Synthetic

<400> SEQUENCE: 6
tagggataac agggagga                   18

<210> SEQ ID NO 7
<211> LENGTH: 22
<212> TYPE: DNA
<213> ORGANISM: Rattus rattus

<400> SEQUENCE: 7
caactgatcc tgagggagtc gg              22

-continued

```
<210> SEQ ID NO 8
<211> LENGTH: 22
<212> TYPE: DNA
<213> ORGANISM: Rattus rattus

<400> SEQUENCE: 8
caaaacgtcg tgagacagtt tg                                              22

<210> SEQ ID NO 9
<211> LENGTH: 22
<212> TYPE: DNA
<213> ORGANISM: Rattus rattus

<400> SEQUENCE: 9
aaaaatgtcc ttgaaggttc ag                                              22

<210> SEQ ID NO 10
<211> LENGTH: 15
<212> TYPE: DNA
<213> ORGANISM: Rattus rattus

<400> SEQUENCE: 10
agacaggggg ctctc                                                      15

<210> SEQ ID NO 11
<211> LENGTH: 7
<212> TYPE: PRT
<213> ORGANISM: Rattus rattus

<400> SEQUENCE: 11

Asn Lys Val Gly Leu Ile Glu
1               5

<210> SEQ ID NO 12
<211> LENGTH: 7
<212> TYPE: PRT
<213> ORGANISM: Rattus rattus

<400> SEQUENCE: 12

Thr Ser Ser Asp Leu Ser Arg
1               5

<210> SEQ ID NO 13
<211> LENGTH: 7
<212> TYPE: PRT
<213> ORGANISM: Rattus rattus

<400> SEQUENCE: 13

Arg Ser Asp His Leu Ser Arg
1               5

<210> SEQ ID NO 14
<211> LENGTH: 7
<212> TYPE: PRT
<213> ORGANISM: Rattus rattus

<400> SEQUENCE: 14

Arg Ser Asp Asn Leu Ser Glu
1               5

<210> SEQ ID NO 15
<211> LENGTH: 7
<212> TYPE: PRT
<213> ORGANISM: Rattus rattus
```

```
<400> SEQUENCE: 15

Gln Asn Ala His Arg Lys Thr
1               5

<210> SEQ ID NO 16
<211> LENGTH: 6
<212> TYPE: PRT
<213> ORGANISM: Rattus rattus

<400> SEQUENCE: 16

Thr Gly Gly Glu Arg Pro
1               5

<210> SEQ ID NO 17
<211> LENGTH: 5
<212> TYPE: PRT
<213> ORGANISM: Rattus rattus

<400> SEQUENCE: 17

Thr Gly Glu Lys Pro
1               5

<210> SEQ ID NO 18
<211> LENGTH: 15
<212> TYPE: DNA
<213> ORGANISM: Rattus rattus

<400> SEQUENCE: 18
aatttggtgg ccatg                                               15

<210> SEQ ID NO 19
<211> LENGTH: 7
<212> TYPE: PRT
<213> ORGANISM: Rattus rattus

<400> SEQUENCE: 19

Arg Ser Asp Ala Leu Ser Thr
1               5

<210> SEQ ID NO 20
<211> LENGTH: 7
<212> TYPE: PRT
<213> ORGANISM: Rattus rattus

<400> SEQUENCE: 20

Asp Arg Ser Thr Arg Thr Lys
1               5

<210> SEQ ID NO 21
<211> LENGTH: 7
<212> TYPE: PRT
<213> ORGANISM: Rattus rattus

<400> SEQUENCE: 21

Arg Ser Asp Ala Leu Ala Arg
1               5

<210> SEQ ID NO 22
<211> LENGTH: 7
<212> TYPE: PRT
<213> ORGANISM: Rattus rattus

<400> SEQUENCE: 22

Arg Ser Asp Ser Leu Ser Ala
```

<210> SEQ ID NO 23
<211> LENGTH: 7
<212> TYPE: PRT
<213> ORGANISM: Rattus rattus

<400> SEQUENCE: 23

Thr Ser Ser Asn Arg Lys Thr
1               5

<210> SEQ ID NO 24
<211> LENGTH: 6
<212> TYPE: PRT
<213> ORGANISM: Rattus rattus

<400> SEQUENCE: 24

Thr Gly Gly Gln Arg Pro
1               5

<210> SEQ ID NO 25
<211> LENGTH: 12
<212> TYPE: DNA
<213> ORGANISM: Rattus rattus

<400> SEQUENCE: 25
gttctggtag tt                                                          12

<210> SEQ ID NO 26
<211> LENGTH: 7
<212> TYPE: PRT
<213> ORGANISM: Rattus rattus

<400> SEQUENCE: 26

Arg Ser Ala Asn Leu Ala Arg
1               5

<210> SEQ ID NO 27
<211> LENGTH: 7
<212> TYPE: PRT
<213> ORGANISM: Rattus rattus

<400> SEQUENCE: 27

Arg Ser Asp Asn Leu Arg Glu
1               5

<210> SEQ ID NO 28
<211> LENGTH: 7
<212> TYPE: PRT
<213> ORGANISM: Rattus rattus

<400> SEQUENCE: 28

Thr Ser Gly Ser Leu Ser Arg
1               5

<210> SEQ ID NO 29
<211> LENGTH: 7
<212> TYPE: PRT
<213> ORGANISM: Rattus rattus

<400> SEQUENCE: 29

Gln Ser Gly Ser Leu Thr Arg
1               5

<210> SEQ ID NO 30
<211> LENGTH: 7
<212> TYPE: PRT
<213> ORGANISM: Rattus rattus

<400> SEQUENCE: 30

Arg Ser Asp Val Leu Ser Glu
1               5

<210> SEQ ID NO 31
<211> LENGTH: 9
<212> TYPE: PRT
<213> ORGANISM: Rattus rattus

<400> SEQUENCE: 31

Thr Gly Gly Gly Gly Ser Gln Arg Pro
1               5

<210> SEQ ID NO 32
<211> LENGTH: 6
<212> TYPE: PRT
<213> ORGANISM: Rattus rattus

<400> SEQUENCE: 32

Thr Gly Ser Gln Lys Pro
1               5

<210> SEQ ID NO 33
<211> LENGTH: 18
<212> TYPE: DNA
<213> ORGANISM: Rattus rattus

<400> SEQUENCE: 33
gaagtcatgc agggtgtc                                              18

<210> SEQ ID NO 34
<211> LENGTH: 7
<212> TYPE: PRT
<213> ORGANISM: Rattus rattus

<400> SEQUENCE: 34

Asp Arg Ser Ala Leu Ser Arg
1               5

<210> SEQ ID NO 35
<211> LENGTH: 7
<212> TYPE: PRT
<213> ORGANISM: Rattus rattus

<400> SEQUENCE: 35

Thr Ser Gly His Leu Ser Arg
1               5

<210> SEQ ID NO 36
<211> LENGTH: 7
<212> TYPE: PRT
<213> ORGANISM: Rattus rattus

<400> SEQUENCE: 36

Arg Ser Asp Asn Leu Ser Thr
1               5

<210> SEQ ID NO 37
<211> LENGTH: 7
<212> TYPE: PRT

<213> ORGANISM: Rattus rattus

<400> SEQUENCE: 37

His Asn Ala Thr Arg Ile Asn
1               5

<210> SEQ ID NO 38
<211> LENGTH: 7
<212> TYPE: PRT
<213> ORGANISM: Rattus rattus

<400> SEQUENCE: 38

Thr Ser Gly Ser Leu Thr Arg
1               5

<210> SEQ ID NO 39
<211> LENGTH: 15
<212> TYPE: DNA
<213> ORGANISM: Rattus rattus

<400> SEQUENCE: 39
ggtgccattg gggtg                                                    15

<210> SEQ ID NO 40
<211> LENGTH: 7
<212> TYPE: PRT
<213> ORGANISM: Rattus rattus

<400> SEQUENCE: 40

Arg Ser Asp His Leu Ser Thr
1               5

<210> SEQ ID NO 41
<211> LENGTH: 7
<212> TYPE: PRT
<213> ORGANISM: Rattus rattus

<400> SEQUENCE: 41

His Ser Asn Ala Arg Lys Asn
1               5

<210> SEQ ID NO 42
<211> LENGTH: 7
<212> TYPE: PRT
<213> ORGANISM: Rattus rattus

<400> SEQUENCE: 42

Glu Arg Gly Thr Leu Ala Arg
1               5

<210> SEQ ID NO 43
<211> LENGTH: 7
<212> TYPE: PRT
<213> ORGANISM: Rattus rattus

<400> SEQUENCE: 43

Gln Ser Gly Asn Leu Ala Arg
1               5

<210> SEQ ID NO 44
<211> LENGTH: 15
<212> TYPE: DNA
<213> ORGANISM: Rattus rattus

<400> SEQUENCE: 44
gctgtgggtg tggct                                                        15

<210> SEQ ID NO 45
<211> LENGTH: 7
<212> TYPE: PRT
<213> ORGANISM: Rattus rattus

<400> SEQUENCE: 45

Gln Ser Ser Asp Leu Ser Arg
1               5

<210> SEQ ID NO 46
<211> LENGTH: 7
<212> TYPE: PRT
<213> ORGANISM: Rattus rattus

<400> SEQUENCE: 46

Arg Ser Asp Ala Leu Thr Gln
1               5

<210> SEQ ID NO 47
<211> LENGTH: 7
<212> TYPE: PRT
<213> ORGANISM: Rattus rattus

<400> SEQUENCE: 47

Arg Ser Asp Ala Leu Ser Arg
1               5

<210> SEQ ID NO 48
<211> LENGTH: 7
<212> TYPE: PRT
<213> ORGANISM: Rattus rattus

<400> SEQUENCE: 48

Asp Arg Ser Asp Leu Ser Arg
1               5

<210> SEQ ID NO 49
<211> LENGTH: 16
<212> TYPE: DNA
<213> ORGANISM: Rattus rattus

<400> SEQUENCE: 49
accatgtgtg gcaggg                                                       16

<210> SEQ ID NO 50
<211> LENGTH: 7
<212> TYPE: PRT
<213> ORGANISM: Rattus rattus

<400> SEQUENCE: 50

Arg Ser Ala His Leu Ser Arg
1               5

<210> SEQ ID NO 51
<211> LENGTH: 7
<212> TYPE: PRT
<213> ORGANISM: Rattus rattus

<400> SEQUENCE: 51

Gln Ser Gly Asp Leu Thr Arg
1               5

```
<210> SEQ ID NO 52
<211> LENGTH: 7
<212> TYPE: PRT
<213> ORGANISM: Rattus rattus

<400> SEQUENCE: 52

Arg Ser Asp Thr Leu Ser Val
1               5

<210> SEQ ID NO 53
<211> LENGTH: 7
<212> TYPE: PRT
<213> ORGANISM: Rattus rattus

<400> SEQUENCE: 53

Asp Asn Ser Thr Arg Ile Lys
1               5

<210> SEQ ID NO 54
<211> LENGTH: 16
<212> TYPE: DNA
<213> ORGANISM: Rattus rattus

<400> SEQUENCE: 54
gaggaccgtg gacaag                                                       16

<210> SEQ ID NO 55
<211> LENGTH: 7
<212> TYPE: PRT
<213> ORGANISM: Rattus rattus

<400> SEQUENCE: 55

Arg Ser Ala Asn Leu Ser Val
1               5

<210> SEQ ID NO 56
<211> LENGTH: 7
<212> TYPE: PRT
<213> ORGANISM: Rattus rattus

<400> SEQUENCE: 56

Asp Arg Ala Asn Leu Ser Arg
1               5

<210> SEQ ID NO 57
<211> LENGTH: 7
<212> TYPE: PRT
<213> ORGANISM: Rattus rattus

<400> SEQUENCE: 57

Arg Ser Asp Asp Leu Thr Arg
1               5

<210> SEQ ID NO 58
<211> LENGTH: 22
<212> TYPE: DNA
<213> ORGANISM: Rattus rattus

<400> SEQUENCE: 58
gttttgcagc actctgtcaa ac                                                22
```

RAT HAVING A DISRUPTED IMMUNOGLOBULIN GENE

CROSS-REFERENCE TO RELATED APPLICATIONS

This application claims priority to U.S. provisional patent application Ser. No. 60/941,619 filed 1 Jun. 2007, and U.S. provisional patent application Ser. No. 61/044,324 filed 11 Apr. 2008, which are incorporated herein in their entirety by reference.

SUMMARY OF THE INVENTION

The invention relates to transgenic animals having one or more inactivated endogenous immunoglobulin loci and methods for making the same. The invention further relates to compositions and methods for the production of humanized and fully human antibodies using such transgenic animals, and antibodies so produced.

BACKGROUND OF THE INVENTION

Antibodies are an important class of pharmaceutical products that have been successfully used in the treatment of various human diseases and conditions, including infectious diseases, cancer, allergic diseases, and graft-versus-host disease, as well as in the prevention of transplant rejection.

One problem associated with the therapeutic application of non-human immunoglobulins is the potential immunogenicity of the same in human patients. In order to reduce the immunogenicity of such preparations, various strategies for the production of partially human (humanized) and fully human antibodies have been developed. The ability to produce transgenic antibodies having a human idiotype in non-human animals is particularly desirable as antigen binding determinants lie within the idiotype region, and non-human idiotypes are thought to contribute to the immunogenicity of current antibody therapeutics. Human idiotype is an especially important consideration in respect of monoclonal antibody therapeutics, which consist of a single idiotype delivered at relatively high concentration as opposed to the variety of idiotypes delivered at lower concentrations by a polyclonal antibody mixture.

While a number of approaches to producing humanized transgenic antibodies in non-human animals have been described, one major problem encountered in many such approaches is the production of endogenous antibody, either preferentially or in combination with transgenic antibodies in the host animal. Various recombinant cloning schemes have been used in attempts to disrupt endogenous immunoglobulin production in host animals to address this problem. However, the functional inactivation of immunoglobulin genes presents many obstacles in many vertebrate species.

For example, while homozygous mutant mice with deleted JH-loci have been successfully produced using homologous recombination, ES or other sustainable pluripotent cells in which homologous recombination can be done to inactivate endogenous loci are not readily available from most vertebrate species.

Further, mutations that interfere with cell surface expression but not with productive rearrangement of immunoglobulin VDJ or VJ gene-segments are insufficient to inactivate endogenous Ig expression completely. This is exemplified by the fact that homozygous mutant mice with a disrupted membrane exon of the μ heavy chain (so called μMT mice) cannot produce IgM or IgG, but still produce significant quantities of IgA (Macpehrson et al. Nature Immunol 2(7):625-631 (2001). In addition, the serum of heterozygous mutant mice contains IgM and IgG encoded by both alleles, the wild-type allele and the mutated μMT allele (Kitamura and Rajewky, Nature 356:154-156 (1992). This is due to the fact that the first rearrangement in the course of B-cell development is the joining of DH- and JH-gene segments on both homologous chromosomes, generating a pro-B cell. If, in the μMT/+ mice, a pro-B cell undergoes subsequent VH-DHJH joining in the mutated IgH locus first and the joining is in frame ("productive"), the resulting pre-B cell can express a μ chain of the secreted form, but cannot express membrane-bound μ. Since membrane-bound μ expression is required for allelic exclusion, such a cell is still able to undergo VH-DHJH joining in the wild-type IgH locus; and if this second rearrangement is also productive, the cell expresses two different μ chains, one of which is membrane-bound. Serum of such mice contains IgM derived from both alleles. In addition, IgG derived from both alleles can be found in the serum of such mice because switching is often concomitantly induced on both IgH loci of a B cell.

Incomplete allelic exclusion is also observed in animals with functional transgenic immunoglobulin loci and mutated endogenous immunoglobulin loci that can still rearrange VDJ or VJ gene segments productively. A B-cell rearranging VH-DHJH in one or both mutated endogenous loci may still rearrange transgenic immunoglobulin loci productively. Such a B-cell expresses membrane-bound transgenic immunoglobulin and develops into a mature B-cell. During B-cell development isotype switching in the mutated endogenous locus may result in a B-cell expressing endogenous immunoglobulin. Accordingly, such mutations are insufficient for the complete inactivation of endogenous immunoglobulin expression in animals with transgenic immunoglobulin loci.

SUMMARY OF THE INVENTION

A major problem associated with the production of humanized transgenic antibodies in non-human animals has been the preferential production or co-production of endogenous antibodies in the host. The current invention solves this problem by providing transgenic animals that harbor at least one artificial Ig locus and lack the capacity to produce endogenous immunoglobulin. These animals are highly useful for the production of humanized and fully human transgenic antibodies. The methods used to generate such transgenic animals are effective in many species, including species from which ES cells or sustainable pluripotent cells are not currently readily available and in which homologous recombination and gene knockouts are not readily done.

The present invention stems in part from the finding that a meganuclease may be used to functionally ablate endogenous immunoglobulin loci to generate transgenic animals useful for the production of humanized and fully human transgenic antibodies. Further, two distinct meganucleases targeting distinct genomic sites may be used to effectively delete a large portion of an immunoglobulin locus (up to several kb), thereby ensuring complete inactivation of the locus and further ensuring that transgenic animals carrying the germline mutation do not generate any B cells capable of endogenous immunoglobulin production.

Accordingly, in one aspect, the invention provides transgenic animals comprising at least one artificial Ig locus and having at least one germline inactivated endogenous Ig locus. The animals used in the invention are small laboratory animals, particularly birds, rodents and weasels. The artificial loci used in the invention comprise at least one human V gene segment. In a preferred embodiment, an artificial Ig locus comprises (i) a V-region having at least one human V gene segment encoding a germline or hypermutated human V-region amino acid sequence; (ii) one or more J gene segments; and (iii) one or more constant region genes, wherein the artificial Ig locus is functional and capable of undergoing gene rearrangement and producing a repertoire of immunoglobulins in the transgenic animal.

In one embodiment, the transgenic animal comprises an inactivated endogenous Ig heavy chain locus. In a preferred embodiment, the transgenic animal has both endogenous Ig heavy chain loci inactivated and accordingly does not carry a functional endogenous Ig heavy chain locus.

In one embodiment, the transgenic animal comprises an inactivated endogenous Ig light chain locus. In a preferred embodiment, the transgenic animal has both endogenous Ig light chain loci inactivated and accordingly does not carry a functional endogenous Ig light chain locus.

In a preferred embodiment, the transgenic animal lacks a functional endogenous Ig heavy chain locus and a functional Ig light chain locus.

In one embodiment, the transgenic animal comprises at least one artificial Ig heavy chain locus. In one embodiment, the transgenic animal lacks a functional Ig light chain locus and comprises at least one artificial Ig heavy chain locus.

In one embodiment, the transgenic animal comprises at least one artificial Ig light chain locus.

In one embodiment, the transgenic animal comprises at least one artificial Ig heavy chain locus and at least one artificial Ig light chain locus.

In a preferred embodiment, artificial Ig loci are functional and capable of undergoing gene rearrangement and producing a repertoire of immunoglobulins in the transgenic animal, which repertoire of immunoglobulins includes immunoglobulins having a human idiotype.

In one embodiment, one or more constant region genes of the artificial Ig loci comprise at least one non-human constant region gene and are functional and capable of undergoing gene rearrangement and producing a repertoire of chimeric immunoglobulins in the transgenic animal, which repertoire of chimeric immunoglobulins includes chimeric immunoglobulins having a human idiotype.

In one embodiment, one or more constant region genes of the artificial Ig loci comprise at least one human constant region gene and are functional and capable of undergoing gene rearrangement and producing a repertoire of immunoglobulins in the transgenic animal, which repertoire of immunoglobulins includes immunoglobulins having a human idiotype and human constant region.

In one aspect, the invention provides descendants of transgenic animals of the invention. In a preferred embodiment, descendants comprise at least one artificial Ig locus and have at least one germline inactivated endogenous Ig locus.

In one aspect, the invention provides transgenic animals capable of generating viable germ cells having at least one endogenous Ig locus that is inactivated.

In one embodiment, such transgenic animals comprise a genomic meganuclease expression construct, preferably a construct having an inducible expression control region operably linked to a meganuclease-encoding nucleic acid, wherein the encoded meganuclease recognizes a meganuclease target sequence present in or proximal to an endogenous Ig locus of the transgenic animal. When the transgenic animal is sexually mature and comprises viable germ cells, the genomic meganuclease expression construct may be used to inactivate the targeted endogenous Ig locus in such germ cells, in vitro or in vivo, without compromising the viability thereof, ensuring F1 animals carrying a germline mutation in an Ig locus may be derived therefrom.

In one embodiment, the transgenic animal further comprises at least one artificial Ig locus.

In one aspect, the invention provides transgenic animals comprising viable germ cells wherein at least one endogenous Ig locus is inactivated. In one embodiment, the transgenic animal further comprises at least one artificial Ig locus.

In one aspect, the invention provides methods for producing transgenic animals of the invention.

In one embodiment, the invention provides methods for producing transgenic animals comprising at least one artificial Ig locus and having at least one germline inactivated endogenous Ig locus. In a preferred embodiment, the transgenic animal is nullizygous for endogenous Ig light chain and/or endogenous Ig heavy chain.

Preferably, an endogenous Ig locus is inactivated in a parent germ cell, or the germ cell of a predecessor, by expression of a meganuclease therein. The methods comprise producing a meganuclease in the germ cell, wherein the meganuclease recognizes a meganuclease target sequence present in or proximal to an endogenous Ig locus and selectively inactivates the targeted Ig locus in the germ cell thereby producing a viable germ cell having at least one inactivated endogenous Ig locus. Such a germ cell having at least one inactivated endogenous Ig locus is used to produce an animal having at least one germline inactivated endogenous Ig locus. In one embodiment, the germ cell, or that which it is combined with, comprises at least one artificial Ig heavy chain locus. In one embodiment, the germ cell, or that which it is combined with, comprises at least one artificial Ig light chain locus. In one embodiment, the germ cell, or that which it is combined with, comprises at least one artificial Ig light chain locus and at least one artificial Ig heavy chain locus.

In one embodiment, the methods involve introducing a meganuclease expression construct or meganuclease-encoding nucleic acid into the germ cell.

In a preferred embodiment, the germ cell comprises a genomic meganuclease expression construct, which comprises an expression control region operably linked to a meganuclease-encoding nucleic acid. In a preferred embodiment, the germ cell comprises an inducible genomic meganuclease expression construct and the methods involve inducing expression of the meganuclease-encoding nucleic acid in the germ cell. In one embodiment, the methods involve repeating the step of inducing expression of the meganuclease-encoding nucleic acid in the germ cell. In one embodiment, induction is done in vivo. In another embodiment, induction is done in vitro. In one embodiment, the germ cell comprises a genomic meganuclease expression construct, which comprises an expression control region that exhibits germ cell-specific activity.

Resultant germ cells may be used to generate an F1 animal having at least one germline inactivated endogenous Ig locus. The F1 animal may comprise one or more artificial Ig loci or may be crossed in order to generate such animals comprising at least one artificial Ig locus.

In an alternative embodiment, the method involves introducing a meganuclease expression construct or meganuclease-encoding nucleic acid into a fertilized oocyte or embryo and generating a viable germ cell having at least one inactivated Ig locus in the resultant founder animal. The founder animal can be used to generate an F1 animal having at least one germline inactivated endogenous Ig locus. The F1 animal may comprise one or more artificial Ig loci or may be crossed in order to generate such animals comprising at least one artificial Ig locus.

In one embodiment, the meganuclease target sequence is present in or proximal to a J gene segment.

In one embodiment, the meganuclease target sequence is present in or proximal to an immunoglobulin constant region gene segment. In a preferred embodiment, the constant region gene encodes immunoglobulin μ.

In one embodiment, the methods involve screening germ cells for viability and inactivation of an endogenous Ig locus. In one embodiment, the methods involve screening germ cells for the presence of an artificial Ig locus.

In methods herein, the crossing of animals is preferably between animals having inactivated endogenous loci, to generate animals that are nullizygous for endogenous Ig light chain and/or endogenous Ig heavy chain.

In a preferred embodiment, the methods further comprise the use of a second meganuclease. The second meganuclease recognizes a second meganuclease target sequence present in or proximal to the endogenous Ig locus and selectively cleaves the endogenous Ig locus together with the first meganuclease but at a site distinct from that of the first meganuclease, thereby inactivating at least one endogenous Ig locus.

In a preferred embodiment, the germ cell comprises a second genomic meganuclease expression construct, which comprises an expression control region operably linked to a second meganuclease-encoding nucleic acid. In a preferred embodiment, the expression control region is an inducible expression control region, and the method further comprises inducing expression of the second meganuclease-encoding nucleic acid in the germ cell, whereby the encoded second meganuclease is produced and, together with the first meganuclease, selectively inactivates the targeted Ig locus in the germ cell. In one embodiment, the methods involve repeating the step of inducing expression of the second meganuclease-encoding nucleic acid in the germ cell. In one embodiment, induction is done in vivo. In one embodiment, induction is done in vitro. In one embodiment, the second genomic meganuclease expression construct comprises an expression control region that exhibits germ cell-specific activity.

In an alternative embodiment, the methods involve introducing a second meganuclease expression construct or second meganuclease-encoding nucleic acid into the germ cell.

In an alternative embodiment, the methods involve introducing a second meganuclease expression construct or second meganuclease-encoding nucleic acid into a fertilized oocyte or embryo and generating a viable germ cell having at least one inactivated Ig locus in the resultant founder animal. The founder animal can be used to generate an F1 animal having at least one germline inactivated endogenous Ig locus. The F1 animal may comprise one or more artificial Ig loci or may be crossed in order to generate such animals comprising at least one artificial Ig locus.

In a preferred embodiment, the first and second meganucleases target J gene segments. In one embodiment, the first and second meganuclease target sequences are, taken together, upstream and downstream of one or more J gene segments within the endogenous Ig locus, and cleavage by the first and second encoded meganucleases produces deletion of a genomic DNA segment comprising the one or more J gene segments.

In another embodiment, the first and second meganucleases target constant region gene segments. In one embodiment, the first and second meganuclease target sequences are, taken together, upstream and downstream of one or more immunoglobulin constant region gene segments, and cleavage by the first and second encoded meganucleases produces deletion of a genomic DNA segment comprising the one or more immunoglobulin constant region gene segments. In a preferred embodiment, the constant region gene encodes immunoglobulin μ.

In methods herein, the artificial loci used comprise at least one human V gene segment. In a preferred embodiment, an artificial Ig locus comprises (i) a V-region having at least one human V gene segment encoding a germline or hypermutated human V-region amino acid sequence; (ii) one or more J gene segments; and (iii) one or more constant region genes, wherein the artificial Ig locus is functional and capable of undergoing gene rearrangement and producing a repertoire of immunoglobulins in the transgenic animal.

In one embodiment, at least one artificial Ig heavy chain locus is incorporated into the genome of a transgenic animal of the invention. In one embodiment, the transgenic animal lacks a functional Ig light chain locus.

In one embodiment, at least one artificial Ig light chain locus is incorporated into the genome of a transgenic animal of the invention.

In one embodiment, at least one artificial Ig heavy chain locus and at least one artificial Ig light chain locus are incorporated into the genome of a transgenic animal of the invention.

In a preferred embodiment, artificial Ig loci are functional and capable of undergoing gene rearrangement and producing a repertoire of immunoglobulins in the transgenic animal, which repertoire of immunoglobulins includes immunoglobulins having a human idiotype.

In one embodiment, one or more constant region genes of the artificial Ig loci comprise at least one non-human constant region gene and are functional and capable of undergoing gene rearrangement and producing a repertoire of chimeric immunoglobulins in the transgenic animal, which repertoire of chimeric immunoglobulins includes chimeric immunoglobulins having a human idiotype.

In one embodiment, one or more constant region genes of the artificial Ig loci comprise at least one human constant region gene and are functional and capable of undergoing gene rearrangement and producing a repertoire of immunoglobulins in the transgenic animal, which repertoire of immunoglobulins includes immunoglobulins having a human idiotype and human constant region.

In one embodiment, the methods of making a transgenic animal of the invention comprise crossing a transgenic animal having at least one germline inactivated endogenous Ig locus with a second transgenic animal having at least one artificial Ig locus, which locus comprises (i) a V-region having at least one human V gene segment encoding a germline or hypermutated human V-region amino acid sequence; (ii) one or more J gene segments; and (iii) one or more constant region genes, to produce an F1 transgenic animal, wherein the F1 transgenic animal comprises the at least one artificial Ig locus of the second transgenic animal, and wherein the artificial Ig locus from the second transgenic animal is functional and capable of undergoing gene rearrangement and producing a repertoire of immunoglobulins in the F1 transgenic animal. The crossing may be done by animal breeding or by otherwise combining gametes, including in vitro manipulations.

In one embodiment, the second transgenic animal comprises at least one artificial Ig heavy chain locus.

In one embodiment, the second transgenic animal comprises at least one artificial Ig light chain locus.

In one embodiment, the first and second transgenic animals lack a functional Ig light chain locus, and the second transgenic animal comprises an artificial Ig heavy chain locus. The animals may be crossed to produce an F1 that lacks a functional Ig light chain locus and comprises an artificial Ig heavy chain locus.

In one embodiment, the second transgenic animal comprises at least two artificial Ig loci, including at least one artificial Ig heavy chain locus and at least one artificial Ig light chain locus. In one embodiment, the artificial Ig loci of the second transgenic animal are functional and capable of undergoing gene rearrangement and producing a repertoire of immunoglobulins in the F1 transgenic animal, which repertoire of immunoglobulins includes immunoglobulins having a human idiotype. In one embodiment, one or more constant region genes of the artificial Ig loci of the second transgenic animal comprise at least one non-human constant region gene and are functional and capable of undergoing gene rearrangement and producing a repertoire of chimeric immunoglobulins in the F1 transgenic animal, which repertoire of chimeric immunoglobulins includes chimeric immunoglobulins having a human idiotype. In one embodiment, one or more constant region genes of the artificial Ig loci of the second transgenic animal comprise at least one human constant region gene and are functional and capable of undergoing gene rearrangement and producing a repertoire of immunoglobulins in the F1 transgenic animal, which repertoire of immunoglobulins includes immunoglobulins having a human idiotype and human constant region.

Similarly, in one embodiment, the methods comprise crossing a second transgenic animal having at least one artificial Ig locus with a transgenic animal of the invention that is capable of generating a viable germ cell having at least one endogenous Ig locus that is inactivated. In a preferred embodiment, the second transgenic animal comprises at least two artificial Ig loci, including at least one artificial Ig heavy chain locus and at least one artificial Ig light chain locus.

In one embodiment, the methods comprise introducing at least one artificial Ig locus into a germ cell having at least one endogenous Ig locus that has been, or is capable of being inactivated by the activity of one or more meganucleases, wherein the at least one artificial Ig locus comprises (i) a V-region having at least one human V gene segment encoding a germline or hypermutated human V-region amino acid sequence; (ii) one or more J gene segments; and (iii) one or more constant region genes, wherein the artificial Ig locus is functional and capable of undergoing gene rearrangement and producing a repertoire of artificial immunoglobulins in a transgenic animal derived from the germ cell. The methods further comprise deriving an F1 transgenic animal comprising at least one artificial Ig locus and having at least one germline inactivated endogenous Ig locus that has been inactivated by the action of one or more meganucleases from the germ cell so produced.

In one embodiment, the at least one artificial Ig locus includes at least one artificial Ig heavy chain locus.

In one embodiment, the germ cell lacks a functional Ig light chain locus and the artificial Ig locus introduced into the germ cell is an Ig heavy chain locus.

In one embodiment, the at least one artificial Ig locus includes at least one artificial Ig light chain locus.

In a preferred embodiment, at least two artificial loci are introduced into the germ cell, including at least one artificial Ig heavy chain locus and at least one artificial Ig light chain locus. In one embodiment, the artificial Ig loci are functional and capable of undergoing gene rearrangement and producing a repertoire of immunoglobulins in the derived F1 transgenic animal, which repertoire of immunoglobulins includes immunoglobulins having a human idiotype. In one embodiment, one or more constant region genes of the artificial Ig loci comprise at least one non-human constant region gene and are functional and capable of undergoing gene rearrangement and producing a repertoire of chimeric immunoglobulins in the derived F1 transgenic animal, which repertoire of chimeric immunoglobulins includes chimeric immunoglobulins having a human idiotype. In one embodiment, one or more constant region genes of the artificial Ig loci comprise at least one human constant region gene and are functional and capable of undergoing gene rearrangement and producing a repertoire of immunoglobulins in the derived F1 transgenic animal, which repertoire of immunoglobulins includes immunoglobulins having a human idiotype and human constant region.

In one embodiment, the methods involve screening germ cells for viability and inactivation of an endogenous Ig locus. In one embodiment, the methods involve screening germ cells for the presence of an artificial Ig locus.

In one embodiment, the methods comprise introducing at least one artificial Ig locus into a fertilized oocyte or embryo derived from a germ cell having at least one endogenous Ig locus that has been inactivated, or is capable of being inactivated, by the action of one or more meganucleases, wherein the at least one artificial Ig locus comprises (i) a V-region having at least one human V gene segment encoding a germline or hypermutated human V-region amino acid sequence; (ii) one or more J gene segments; and (iii) one or more constant region genes, wherein the artificial Ig locus is functional and capable of undergoing gene rearrangement and producing a repertoire of artificial immunoglobulins in the founder transgenic animal, or a descendant thereof, derived from the fertilized oocyte or embryo. The methods further comprise deriving from the fertilized oocyte or embryo the founder transgenic animal, and optionally the descendant thereof, to yield a transgenic animal comprising at least one artificial Ig locus and having at least one germline inactivated endogenous Ig locus that has been inactivated by the action of one or more meganucleases.

In one embodiment, the at least one artificial Ig locus includes at least one artificial Ig heavy chain locus.

In one embodiment, the at least one artificial Ig locus includes at least one artificial Ig light chain locus.

In one embodiment, the fertilized oocyte or embryo lacks a functional Ig light chain locus, and the artificial Ig locus introduced into the fertilized oocyte or embryo is an Ig heavy chain locus.

In a preferred embodiment, at least two artificial loci are introduced into the fertilized oocyte or embryo, including at least one artificial Ig heavy chain locus and at least one artificial Ig light chain locus. In one embodiment, the artificial Ig loci are functional and capable of undergoing gene rearrangement and producing a repertoire of immunoglobulins in the founder transgenic animal, or a descendant thereof, which repertoire of immunoglobulins includes immunoglobulins having a human idiotype. In one embodiment, one or more constant region genes of the artificial Ig loci comprise at least one non-human constant region gene and are functional and capable of undergoing gene rearrangement and producing a repertoire of chimeric immunoglobulins in the founder transgenic animal, or a descendant thereof, which repertoire of chimeric immunoglobulins includes chimeric immunoglobulins having a human idiotype. In one embodiment, one or more constant region genes of the artificial Ig loci comprise at least one human constant region gene and are functional and capable of undergoing gene rearrangement and producing a repertoire of immunoglobulins in the founder transgenic animal, or a descendant thereof, which repertoire of immunoglobulins includes immunoglobulins having a human idiotype and human constant region.

In one aspect, the invention provides methods for producing transgenic animals capable of generating a viable germ cell wherein at least one endogenous Ig locus is inactivated. In a preferred embodiment, the methods comprise generating a transgenic animal having a genomic meganuclease expression construct, wherein the expression construct comprises an expression control region operably linked to a meganuclease-encoding nucleic acid. In a preferred embodiment, the construct is an inducible genomic meganuclease expression construct that can be induced to express the meganuclease-encoding nucleic acid in a germ cell In one aspect, the invention provides methods for producing a transgenic animal having a viable germ cell wherein at least one endogenous Ig locus is inactivated. The methods comprise inactivating the endogenous Ig locus in the germ cell, or in a parent germ cell or fertilized oocyte or embryo derived therefrom, by expression of a meganuclease therein.

In one aspect, the invention provides a viable germ cell wherein at least one endogenous Ig locus is capable of being inactivated. In a preferred embodiment, the germ cell comprises a genomic meganuclease expression construct, wherein the expression construct comprises an expression control region operably linked to a meganuclease-encoding nucleic acid. In a preferred embodiment, the construct is an inducible genomic meganuclease expression construct that can be induced to express the meganuclease-encoding nucleic acid in a germ cell.

In one embodiment, the germ cell comprises at least one artificial Ig heavy chain locus.

In one embodiment, the germ cell comprises at least one artificial Ig light chain locus.

In one embodiment, the germ cell comprises at least one artificial Ig heavy chain locus and at least one artificial Ig light chain locus.

In one aspect, the invention provides a viable germ cell wherein at least one endogenous Ig locus is inactivated.

In one embodiment, the germ cell comprises at least one artificial Ig heavy chain locus.

In one embodiment, the germ cell comprises at least one artificial Ig light chain locus.

In one embodiment, the germ cell comprises at least one artificial Ig heavy chain locus and at least one artificial Ig light chain locus.

In one aspect, the invention provides methods for producing a viable germ cell having at least one inactivated endogenous Ig locus. The methods involve expressing at least one meganuclease in a germ cell, fertilized oocyte or embryo, to generate a viable germ cell having at least one inactivated endogenous Ig locus. The meganuclease so expressed recognizes a meganuclease target sequence present in or proximal to said endogenous Ig locus.

In one embodiment, wherein the meganuclease is expressed in a germ cell, the germ cell in which the meganuclease is expressed yields a viable germ cell having at least one inactivated endogenous Ig locus. Alternatively, a viable germ cell having at least one inactivated endogenous Ig locus may be obtained from an animal derived from the germ cell in which the meganuclease was expressed.

In one embodiment, wherein the meganuclease is expressed in a fertilized oocyte or embryo, the viable germ cell having at least one inactivated endogenous Ig locus may be obtained from an animal derived from the fertilized oocyte or embryo in which the meganuclease was expressed.

In one embodiment, the at least one endogenous Ig locus is inactivated in vitro. In one embodiment, the at least one endogenous Ig locus is inactivated in vivo.

In one embodiment, the germ cell further comprises at least one artificial Ig locus. In one embodiment, the at least one artificial Ig locus includes at least one artificial Ig heavy chain locus. In one embodiment, the at least one artificial Ig locus includes at least one artificial Ig light chain locus.

In one embodiment, at least two artificial Ig loci are introduced into the germ cell, including at least one artificial Ig heavy chain locus and at least one artificial Ig light chain locus.

The invention also provides polyclonal antibodies, monoclonal antibodies; hybridomas, and methods of making and using the same, which stem from the production of antibodies in the presently disclosed transgenic animals carrying one or more artificial loci and having one or more endogenous Ig loci inactivated by way of meganuclease activity.

In one embodiment, the antibodies are heavy chain-only antibodies, which are produced using transgenic animals which lack a functional Ig light chain locus and comprise an artificial heavy chain locus, achieved by methods described herein.

In one aspect, the invention provides methods for producing antibodies using transgenic animals provided herein. The methods comprise immunizing a transgenic animal of the invention, which animal has at least one inactivated endogenous Ig locus and carries at least one artificial Ig locus as described herein, with an immunogen. In a preferred embodiment, the transgenic animal is nullizygous for endogenous Ig heavy chain and/or endogenous Ig light chain and, accordingly, incapable of producing endogenous immunoglobulins. In one embodiment, the transgenic animal lacks a functional Ig light chain locus and comprises an artificial Ig heavy chain locus.

In one aspect, the invention provides polyclonal antisera compositions so produced. Polyclonal antisera of the invention preferably comprise antibodies having a human idiotype. In a preferred embodiment, a polyclonal antiserum comprises antibodies that consist essentially of antibodies having a human idiotype.

In one aspect, the invention provides methods for producing monoclonal antibodies.

In one embodiment, the methods comprise (i) immunizing a transgenic animal of the invention, which animal has at least one inactivated endogenous Ig locus and carries at least one artificial Ig locus as described herein, with an immunogen, (ii) isolating a monoclonal antibody producing cell from the transgenic animal wherein the monoclonal antibody producing cell produces a monoclonal antibody that specifically binds to the immunogen; and (iii) using the monoclonal antibody producing cell to produce the monoclonal antibody that specifically binds to the immunogen, or using the monoclonal antibody producing cell to produce a hybridoma cell that produces the monoclonal antibody and using the hybridoma cell to produce the monoclonal antibody.

In one embodiment, the methods comprise (i) immunizing a transgenic animal of the invention, which animal has at least one inactivated endogenous Ig locus and carries at least one artificial Ig locus as described herein, with an immunogen; (ii) isolating a monoclonal antibody producing cell from the transgenic animal wherein the monoclonal antibody producing cell produces a monoclonal antibody that specifically binds to the immunogen; (iii) isolating from the monoclonal antibody producing cell a monoclonal antibody nucleic acid which encodes the monoclonal antibody that specifically binds to the immunogen; and (iv) using the monoclonal antibody nucleic acid to produce the monoclonal antibody that specifically binds to the immunogen.

In a preferred embodiment, the monoclonal antibody has a human idiotype.

In one aspect, the invention provides monoclonal antibodies so produced.

In one aspect, the invention provides isolated nucleic acids encoding such monoclonal antibodies.

In one aspect, the invention provides methods for producing fully human monoclonal antibodies. The methods comprise (i) immunizing a transgenic animal of the invention, which animal has at least one inactivated endogenous Ig locus and carries at least one artificial Ig locus as described herein, with an immunogen; (ii) isolating a monoclonal antibody producing cell from the transgenic animal wherein the monoclonal antibody producing cell produces a monoclonal antibody that specifically binds to the immunogen; (iii) isolating from the monoclonal antibody producing cell a monoclonal antibody nucleic acid which encodes the monoclonal antibody that specifically binds to the immunogen; (iv) modifying the monoclonal antibody nucleic acid to produce a recombinant nucleic acid encoding a fully human monoclonal antibody; and (v) using the recombinant nucleic acid encoding a fully human monoclonal antibody to produce the encoded fully human monoclonal antibody.

In one aspect, the invention provides fully human monoclonal antibodies so produced.

In one aspect, the invention provides recombinant nucleic acids encoding fully human monoclonal antibodies, and methods of producing the same.

In one embodiment, an immunogen used in methods herein comprises a disease-causing organism or antigenic portion thereof.

In one embodiment, an immunogen used in methods herein is an antigen endogenous to humans. In an alternative embodiment, an immunogen used in methods herein is an antigen exogenous to humans.

In one aspect, the invention provides methods for neutralizing or modulating the activity of an antigenic entity in a human body component. In one embodiment, the methods comprise contacting the body component with a polyclonal antisera composition of the invention, wherein the polyclonal antisera composition comprises immunoglobulin molecules that specifically bind to and neutralize or modulate the activity of the antigenic entity.

In one embodiment, the methods comprise contacting the body component with a monoclonal antibody of the invention, wherein the monoclonal antibody specifically binds to and neutralizes or modulates the activity of the antigenic entity.

In a preferred embodiment, the monoclonal antibody is a fully human monoclonal antibody.

In one embodiment, the antigenic entity is from an organism that causes an infectious disease.

In one embodiment, the antigenic entity is a cell surface molecule.

In one embodiment, the antigenic entity is a human cytokine or a human chemokine.

In one embodiment, the antigenic entity is a cell surface molecule on a malignant cancer cell.

In one aspect, the invention provides cells derived from transgenic animals of the invention.

In a preferred embodiment, the invention provides cells derived from the spleen of transgenic animals of the invention.

In a preferred embodiment, the invention provides B cells derived from transgenic animals of the invention, which B cells are capable of producing antibodies having a human idiotype.

In a preferred embodiment, the invention provides germ cells derived from transgenic animals of the invention.

In one aspect, the invention provides methods for making hybridomas capable of producing antibodies having a human idiotype. The methods comprise the use of cells derived from transgenic animals of the invention.

In one aspect, the invention provides hybridomas so produced.

In one aspect, the invention provides antibodies having a human idiotype, which antibodies are produced by a hybridoma of the invention.

In one aspect, the invention provides pharmaceutical compositions comprising an antibody of the invention, which antibody has a human idiotype.

In one aspect, the invention provides methods of treating a patient in need of treatment, comprising administering a therapeutically effective amount of a pharmaceutical composition of the invention to the patient.

DETAILED DESCRIPTION OF THE INVENTION

Figure 1:
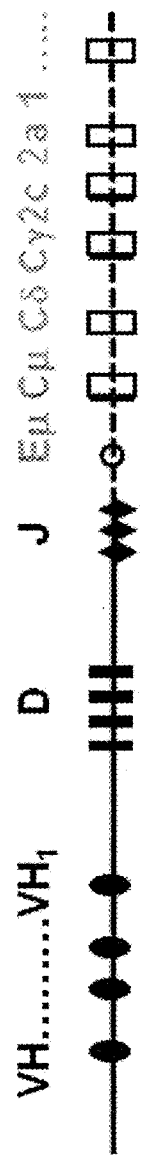
FIG. 1 shows a schematic representation of an artificial heavy chain consisting of a human V-, D-, and J-region, a rat intronic enhancer and several artificial constant region genes. Artificial constant region genes contain exons encoding a human CH1 domain and rat CH2, 3 and 4 domains. Membrane spanning and cytoplasmic polypeptide sequences are encoded by rat exons.

By "artificial immunoglobulin locus" is meant an immunoglobulin locus comprising fragments of human and non-human immunoglobulin loci, including multiple immunoglobulin gene segments, which include at least one variable region (V) gene segment, one or more J gene segments, one or more D gene segments in the case of a heavy chain locus, and one or more constant region gene segments. In the present invention, at least one of the V gene segments encodes a germline or hypermutated human V-region amino acid sequence. In a preferred embodiment, an artificial immunoglobulin locus of the invention is functional and capable of rearrangement and producing a repertoire of immunoglobulins. In a preferred embodiment, at least one D gene segment is a human D gene segment. "Artificial Ig locus" as used herein can refer to unrearranged loci, partially rearranged loci, and rearranged loci. Artificial Ig loci include artificial Ig light chain loci and artificial Ig heavy chain loci. In one embodiment, an artificial Ig locus comprises a non-human C region gene and is capable of producing a repertoire of immunoglobulins including chimeric immunoglobulins having a non-human C region. In one embodiment, an artificial Ig locus comprises a human C region gene and is capable of producing a repertoire of immunoglobulins including immunoglobulins having a human C region. In one embodiment, an artificial Ig locus comprises an "artificial constant region gene", by which is meant a constant region gene comprising nucleotide sequences derived from human and non-human constant regions genes. For example, an exemplary artificial C constant region gene is a constant region gene encoding a human IgG CH1 domain and rat IgG CH2 and CH3 domain.

In some embodiments, an artificial Ig heavy chain locus lacks CH1, or an equivalent sequence that allows the resultant immunoglobulin to circumvent the typical immunoglobulin:chaperone association. Such artificial loci provide for the production of heavy chain-only antibodies in transgenic animals which lack a functional Ig light chain locus and hence do not express functional Ig light chain. Such artificial Ig heavy chain loci are used in methods herein to produce transgenic animals lacking a functional Ig light chain locus, and comprising an artificial Ig heavy chain locus, which animals are capable of producing heavy chain-only antibodies. Alternatively, an artificial Ig locus may be manipulated in situ to disrupt CH1 or an equivalent region and generate an artificial Ig heavy chain locus that provides for the production of heavy chain-only antibodies. Regarding the production of heavy chain-only antibodies in light chain-deficient mice, see for example Zou et al., JEM, 204:3271-3283, 2007.

By "human idiotype" is meant a polypeptide sequence present on a human antibody encoded by an immunoglobulin V-gene segment. The term "human idiotype" as used herein includes both naturally occurring sequences of a human antibody, as well as synthetic sequences substantially identical to the polypeptide found in naturally occurring human antibodies. By "substantially" is meant that the degree of amino acid sequence identity is at least about 85%-95%. Preferably, the degree of amino acid sequence identity is greater than 90%, more preferably greater than 95%.

By a "chimeric antibody" or a "chimeric immunoglobulin" is meant an immunoglobulin molecule comprising a portion of a human immunoglobulin polypeptide sequence (or a polypeptide sequence encoded by a human Ig gene segment) and a portion of a non-human immunoglobulin polypeptide sequence. The chimeric immunoglobulin molecules of the present invention are immunoglobulins with non-human Fc-regions or artificial Fc-regions, and human idiotypes. Such immunoglobulins can be isolated from animals of the invention that have been engineered to produce chimeric immunoglobulin molecules.

By "artificial Fc-region" is meant an Fc-region encoded by an artificial constant region gene.

The term "Ig gene segment" as used herein refers to segments of DNA encoding various portions of an Ig molecule, which are present in the germline of non-human animals and humans, and which are brought together in B cells to form rearranged Ig genes. Thus, Ig gene segments as used herein include V gene segments, D gene segments, J gene segments and C region gene segments.

The term "human Ig gene segment" as used herein includes both naturally occurring sequences of a human Ig gene segment, degenerate forms of naturally occurring sequences of a human Ig gene segment, as well as synthetic sequences that encode a polypeptide sequence substantially identical to the polypeptide encoded by a naturally occurring sequence of a human Ig gene segment. By "substantially" is meant that the degree of amino acid sequence identity is at least about 85%-95%. Preferably, the degree of amino acid sequence identity is greater than 90%, more preferably greater than 95%.

By "meganuclease" is meant an endodeoxyribonuclease that recognizes long recognition sites in DNA, preferably at least 12, more preferably at least 13, more preferably at least 14, more preferably at least 15, more preferably at least 16, more preferably at least 17, and most preferably at least 18 nucleotides in length. Meganucleases include zinc-finger nucleases, naturally occurring homing endonucleases and custom engineered zinc-finger nucleases and homing endonucleases. What is required for use in the invention is that the meganuclease recognize a meganuclease target sequence present in or proximal to an endogenous Ig locus in the subject animal such that a functional mutation may be introduced in the Ig locus by the action of the meganuclease. For more discussion of meganucleases, see, for example, U.S. Patent Application Publication Nos. 20060206949, 20060153826, 20040002092, 20060078552, and 20050064474.

Zinc-finger nucleases with altered specificity can be generated by combining individual zinc fingers with different triplet targets. The specificity of naturally occurring homing endonucleases can be altered by structure-based protein engineering. For example, see Proteus and Carroll, nature biotechnology 23(8):967-97, 2005.

An animal having a "germline inactivated Ig locus", or "germline inactivated endogenous Ig locus", or "germline mutation in an endogenous Ig locus", has an inactivated endogenous Ig locus in every cell, i.e., every somatic and germ cell. In the present invention, animals having germline inactivated loci are produced by mutation, as effected by the action of a meganuclease in a germ cell which gives rise to the resultant animal, or a predecessor thereof.

Production of Viable Germ Cells and Transgenic Animals Having Inactivated Endogenous Ig Loci In the present invention, meganucleases are used to inactivate endogenous Ig loci so as to produce viable germ cells having at least one inactivated endogenous Ig locus. The methods involve expressing at least one meganuclease in a germ cell, fertilized oocyte or embryo, to generate a viable germ cell having at least one inactivated endogenous Ig locus. The meganuclease so expressed recognizes a meganuclease target sequence present in or proximal to an endogenous Ig locus in the subject animal.

In one embodiment, wherein the meganuclease is expressed in a germ cell, the germ cell in which the meganuclease is expressed yields a viable germ cell having at least one inactivated endogenous Ig locus. Alternatively, a viable germ cell having at least one inactivated endogenous Ig locus may be obtained from an animal derived from the germ cell in which the meganuclease was expressed.

In one embodiment, wherein the meganuclease is expressed in a fertilized oocyte or embryo, the viable germ cell having at least one inactivated endogenous Ig locus may be obtained from an animal derived from the fertilized oocyte or embryo in which the meganuclease was expressed.

The invention also provides methods for producing transgenic animals comprising at least one germline inactivated endogenous Ig locus. The methods comprise deriving a transgenic animal from a viable germ cell having at least one inactivated endogenous Ig locus produced according to the methods herein.

In one embodiment, the viable germ cell having at least one inactivated endogenous Ig locus further comprises an artificial Ig locus, and the transgenic animal so produced comprises an artificial Ig locus.

In one embodiment, the methods further comprise introducing an artificial Ig locus into the viable germ cell having at least one inactivated endogenous Ig locus, or a germ cell descendant thereof or a fertilized oocyte or embryo derived therefrom, and the transgenic animal so produced comprises an artificial Ig locus.

In one embodiment, the methods comprise combining a viable germ cell having at least one inactivated endogenous Ig locus, or a germ cell descendant thereof, with a gamete comprising an artificial Ig locus, and the transgenic animal so produced comprises an artificial Ig locus.

Inactivation of Endogenous Ig Loci

Inactivation of endogenous Ig loci is done using meganucleases specific for immunoglobulin gene fragments in heavy and/or light chain loci endogenous to the subject animal. In one embodiment double-strand breaks may be induced by injection of a meganuclease into germ cells, fertilized oocytes or embryos. Alternatively, expression vectors or nucleic acid encoding a meganuclease and capable of being expressed in germ cells, fertilized oocytes or embryos may be injected into the same.

In one embodiment, the method involves transfecting germ cells, which may include precursors thereof such as spermatagonial stem cells, in vitro or in vivo with a meganuclease encoding nucleic acid or expression construct. For example, see Ryu et al., J. Androl., 28:353-360, 2007; Orwig et al., Biol. Report, 67:874-879, 2002.

In a preferred embodiment, a meganuclease expression construct is integrated into the genome of the subject animal. Expression of the transgene encoding the meganuclease in germ cells will result in double-strand breaks in endogenous Ig loci and subsequent mutation of the restriction site. Mating of such transgenic animals results in offspring with mutated/inactivated immunoglobulin loci.

In a highly preferred embodiment of the present invention, a regulatable meganuclease expression construct is integrated into the genome of the subject animal, which regulatable construct is inducible in germ cells. Such constructs provide for minimization of cytotoxic effects associated with expression of a particular meganuclease through controlled expression via inducible promoters, e.g., heat-inducible promoters, radiation-inducible promoters, tetracycline operon, hormone inducible promoters, and promoters inducible by dimerization of transactivators, and the like. For example, see Vilaboa et al., Current Gene Therapy, 6:421-438, 2006.

Alternatively, meganuclease expression may be induced in an embryo derived from the germ cell.

In one embodiment, a single meganuclease is expressed in a germ cell, wherein the meganuclease recognizes a target sequence in or proximal to an immunoglobulin locus endogenous to the germ cell of the subject animal. In a preferred embodiment, the meganuclease target sequence is in or proximal to a J gene segment. In another preferred embodiment, the meganuclease target sequence is in or proximal to an immunoglobulin constant region gene. In a preferred embodiment, the immunoglobulin constant region gene encodes immunoglobulin μ.

In a preferred embodiment, at least two meganucleases having distinct target sequences are used. The at least two meganucleases are expressed in a germ cell, wherein the meganucleases recognize distinct target sequences in or proximal to an immunoglobulin locus endogenous to the germ cell of the subject animal.

In a preferred embodiment, the first and second meganucleases target J gene segments. In one embodiment, the first and second meganuclease target sequences are, taken together, upstream and downstream of one or more J gene segments within the endogenous Ig locus, and cleavage by the first and second encoded meganucleases produces deletion of a genomic DNA segment comprising the one or more J gene segments.

In another embodiment, the first and second meganucleases target constant region gene segments. In one embodiment, the first and second meganuclease target sequences are, taken together, upstream and downstream of one or more immunoglobulin constant region gene segments, and cleavage by the first and second encoded meganucleases produces deletion of a genomic DNA segment comprising the one or more immunoglobulin constant region gene segments. In a preferred embodiment, the constant region gene encodes immunoglobulin μ.

In one embodiment, an entire endogenous Ig heavy chain and/or Ig light chain locus, or large parts thereof are deleted from the genome of the subject animal. Such animals are also referred to as comprising an endogenous locus that has been inactivated.

In one embodiment, at least one meganuclease is used to disrupt the CH1 region of an endogenous Ig heavy chain locus, leaving the remainder of the locus intact and capable of producing an Ig heavy chain that circumvents the typical immunoglobulin:chaperone association. Preferably, this CH1 targeting is done in an animal lacking a functional Ig light chain locus. Such targeting in such animals is useful for producing heavy chain-only antibodies.

In one embodiment, more than one meganuclease is used to target CH1 within the Ig heavy chain locus.

In one embodiment, two meganucleases recognizing adjacent sites are used. In one embodiment, the sites are elements of a palindrome. In one embodiment, the two meganucleases are tethered by a linker.

In preferred embodiments, the breeding strategies used are designed to obtain animals that are nullizygous for endogenous Ig light chain and/or endogenous Ig heavy chain.

Transgenic Animals Comprising Regulatable Genomic Meganuclease Expression Constructs In one aspect, the invention provides transgenic animals comprising at least one regulatable genomic meganuclease expression construct.

The transgenic animals are selected from small laboratory animals, particularly birds (chicken, turkey, quail, duck, pheasant or goose and the like), rodents (e.g., rats, hamsters and guinea pigs), and weasels (e.g., ferrets).

In a preferred embodiment, the regulatable genomic meganuclease expression construct comprises an inducible expression control region operably linked to a meganuclease-encoding nucleic acid. The inducible expression control region is inducibly functional in a germ cell of the particular transgenic animal, and the encoded meganuclease is selective for a meganuclease target sequence situated in or proximal to an endogenous immunoglobulin locus of the subject animal.

A regulatable meganuclease expression construct provides for minimization of cytotoxic effects associated with expression of a particular meganuclease through controlled expression via inducible promoters, e.g., heat-inducible promoters, radiation-inducible promoters, tetracycline operon, hormone inducible promoters, and promoters inducible by dimerization of transactivators, and the like.

In a preferred embodiment, a transgenic animal of the invention comprises two regulatable genomic meganuclease expression constructs, comprising two distinct nucleic acids encoding two distinct meganucleases that recognize two distinct target sequences. The two meganucleases in combination function to delete a genomic DNA segment of an endogenous Ig locus and thereby inactivate the same.

Transgenic animals comprising at least one regulatable genomic meganuclease expression construct may be made by means well known in the art. For example, a transgenic vector containing an inducible expression control region operably linked to a meganuclease-encoding nucleic acid may be introduced into a recipient cell or cells and then integrated into the genome of the recipient cell or cells by random integration or by targeted integration.

For random integration, such a transgenic vector can be introduced into a recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells or other pluripotent cells (for example primordial germ cells) and subsequently injecting the genetically modified cells into developing embryos. Alternatively, a transgenic vector (naked or in combination with facilitating reagents) can be directly injected into a developing embryo. In another embodiment, the transgenic vector is introduced into the genome of a cell and an animal is derived from the transfected cell by nuclear transfer cloning.

For targeted integration, such a transgenic vector can be introduced into appropriate recipient cells such as embryonic stem cells or already differentiated somatic cells. Afterwards, cells in which the transgene has integrated into the animal genome at the targeted site by homologous recombination can be selected by standard methods. The selected cells may then be fused with enucleated nuclear transfer unit cells, e.g. oocytes or embryonic stem cells, cells which are totipotent and capable of forming a functional neonate. Fusion is performed in accordance with conventional techniques which are well established. See, for example, Cibelli et al., Science (1998) 280:1256 Zhou et al. Science (2003) 301: 1179. Enucleation of oocytes and nuclear transfer can also be performed by microsurgery using injection pipettes. (See, for example, Wakayama et al., Nature (1998) 394:369.) The resulting cells are then cultivated in an appropriate medium, and transferred into synchronized recipients for generating transgenic animals. Alternatively, the selected genetically modified cells can be injected into developing embryos.

In one embodiment, a meganuclease is used to increase the frequency of homologous recombination at a target site through double-strand DNA cleavage.

Transgenic Animals Comprising Artificial Ig Loci and Capable of Producing Antibodies Having Human Idiotypes In one aspect, the invention provides transgenic animals capable of producing immunoglobulins having human idiotypes, as well as methods of making the same.

The transgenic animals used are selected from particularly birds (chicken, turkey, quail, duck, pheasant or goose and the like), rodents (e.g., rats, hamsters and guinea pigs), and weasels (e.g., ferrets).

The transgenic animals used for humanized antibody production in the invention carry germline mutations in endogenous Ig loci that have been effected by the activity of one or more meganucleases. In a preferred embodiment, the transgenic animals are nullizygous for endogenous Ig heavy chain and/or endogenous Ig light chain. Further, these animals carry at least one artificial Ig locus that is functional and capable of producing a repertoire of immunoglobulin molecules in the transgenic animal. The artificial Ig loci used in the invention include at least one human V gene segment.

In a preferred embodiment, the transgenic animals carry at least one artificial Ig heavy chain locus and at least one artificial Ig light chain locus that are each functional and capable of producing a repertoire of immunoglobulin molecules in the transgenic animal, which repertoire of immunoglobulin molecules includes antibodies having a human idiotype. In one embodiment, artificial loci including at least one non-human C gene are used, and animals capable of producing chimeric antibodies having a human idiotype and non-human constant region are provided. In one embodiment, artificial loci including at least one human C gene are used, and animals capable of producing antibodies having a human idiotype and human constant region are provided.

In another preferred embodiment, the transgenic animals carry at least one artificial Ig heavy chain locus, and lack a functional Ig light chain locus. Such animals find use in the production of heavy chain-only antibodies.

Production of such transgenic animals involves the integration of one or more artificial heavy chain Ig loci and one or more artificial light chain Ig loci into the genome of a transgenic animal having at least one endogenous Ig locus that has been or will be inactivated by the action of one or more meganucleases. Preferably, the transgenic animals are nullizygous for endogenous Ig heavy chain and/or endogenous Ig light chain and, accordingly, incapable of producing endogenous immunoglobulins. Regardless of the chromosomal location, an artificial Ig locus of the present invention has the capacity to undergo gene rearrangement and thereby produce a diversified repertoire of immunoglobulin molecules. An Ig locus having the capacity to undergo gene rearrangement is also referred to herein as a "functional" Ig locus, and the antibodies with a diversity generated by a functional Ig locus are also referred to herein as "functional" antibodies or a "functional" repertoire of antibodies.

The artificial loci used to generate such transgenic animals each include multiple immunoglobulin gene segments, which include at least one V region gene segment, one or more J gene segments, one or more D gene segments in the case of a heavy chain locus, and one or more constant region genes. In the present invention, at least one of the V gene segments encodes a germline or hypermutated human V-region amino acid sequence. Accordingly, such transgenic animals have the capacity to produce a diversified repertoire of immunoglobulin molecules, which include antibodies having a human idiotype.

In one embodiment, the artificial loci used comprise at least one non-human C region gene segment. Accordingly, such transgenic animals have the capacity to produce a diversified repertoire of immunoglobulin molecules, which include chimeric antibodies having a human idiotype.

In one embodiment, the artificial loci used comprise at least one human C region gene segment. Accordingly, such transgenic animals have the capacity to produce a diversified repertoire of immunoglobulin molecules, which include antibodies having a human idiotype and a human constant region.

In one embodiment, the artificial loci used comprise at least one artificial constant region gene. For example, an exemplary artificial C constant region gene is a constant region gene encoding a human IgG CH1 domain and rat IgG CH2 and CH3 domain. Accordingly, such transgenic animals have the capacity to produce a diversified repertoire of immunoglobulin molecules, which include antibodies having a human idiotype and an artificial constant region comprising both human and non-human components.

The transgenic vector containing an artificial Ig locus is introduced into the recipient cell or cells and then integrated into the genome of the recipient cell or cells by random integration or by targeted integration.

For random integration, a transgenic vector containing an artificial Ig locus can be introduced into a recipient cell by standard transgenic technology. For example, a transgenic vector can be directly injected into the pronucleus of a fertilized oocyte. A transgenic vector can also be introduced by co-incubation of sperm with the transgenic vector before fertilization of the oocyte. Transgenic animals can be developed from fertilized oocytes. Another way to introduce a transgenic vector is by transfecting embryonic stem cells or other pluripotent cells (for example primordial germ cells) and subsequently injecting the genetically modified cells into developing embryos. Alternatively, a transgenic vector (naked or in combination with facilitating reagents) can be directly injected into a developing embryo. Ultimately, chimeric transgenic animals are produced from the embryos which contain the artificial Ig transgene integrated in the genome of at least some somatic cells of the transgenic animal. In another embodiment, the transgenic vector is introduced into the genome of a cell and an animal is derived from the transfected cell by nuclear transfer cloning.

In a preferred embodiment, a transgene containing an artificial Ig locus is randomly integrated into the genome of recipient cells (such as fertilized oocyte or developing embryos). The recipient cells are derived from an animal having at least one endogenous Ig locus that has been inactivated by the action of one or more meganucleases. Alternatively, transgenic animals carrying artificial immunoglobulin loci, can be crossed with transgenic animals having at least one endogenous Ig locus that has been inactivated by the action of one or more meganucleases. Regardless of the particular method used, in a preferred embodiment, offspring that are nullizygous for endogenous Ig heavy chain and/or Ig light chain and, accordingly, incapable of producing endogenous immunoglobulins and capable of producing transgenic immunoglobulins are obtained.

For targeted integration, a transgenic vector can be introduced into appropriate recipient cells such as embryonic stem cells, other pluripotent cells or already differentiated somatic cells. Afterwards, cells in which the transgene has integrated into the animal genome and has replaced the corresponding endogenous Ig locus by homologous recombination can be selected by standard methods. The selected cells may then be fused with enucleated nuclear transfer unit cells, e.g. oocytes or embryonic stem cells, cells which are totipotent and capable of forming a functional neonate. Fusion is performed in accordance with conventional techniques which are well established. See, for example, Cibelli et al., Science (1998) 280:1256; Zhou et al. Science (2003) 301: 1179. Enucleation of oocytes and nuclear transfer can also be performed by microsurgery using injection pipettes. (See, for example, Wakayama et al., Nature (1998) 394:369.) The resulting cells are then cultivated in an appropriate medium, and transferred into synchronized recipients for generating transgenic animals. Alternatively, the selected genetically modified cells can be injected into developing embryos which are subsequently developed into chimeric animals.

In one embodiment, a meganuclease is used to increase the frequency of homologous recombination at a target site through double-strand DNA cleavage. For integration into endogenous immunoglobulin loci a site specific meganuclease may be used. In one embodiment, a meganuclease targeting an endogenous Ig locus is used to increase the frequency of homologous recombination and replacement of an endogenous Ig locus, or parts thereof with an artificial Ig locus, or parts thereof.

In one embodiment, the transgenic animal lacks a functional Ig light chain locus and comprises an artificial Ig heavy chain locus.

Artificial Ig Loci

The present invention is further directed to artificial Ig loci and their use in making transgenic animals capable of producing immunoglobulins having a human idiotype.

Each artificial Ig locus comprises multiple immunoglobulin gene segments, which include at least one V region gene segment, one or more J gene segments, one or more D gene segments in the case of a heavy chain locus, and one or more constant region genes. In the present invention, at least one of the V gene segments encodes a germline or hypermutated human V-region amino acid sequence. Accordingly, such transgenic animals have the capacity to produce a diversified repertoire of immunoglobulin molecules, which include antibodies having a human idiotype. In heavy chain loci human or non-human-derived D-gene segments may be included in the artificial Ig loci. The gene segments in such loci are juxtaposed with respect to each other in an unrearranged configuration (or "the germline configuration"), or in a partially or fully rearranged configuration. The artificial Ig loci have the capacity to undergo gene rearrangement (if the gene segments are not fully rearranged) in the subject animal thereby producing a diversified repertoire of immunoglobulins having human idiotypes.

Regulatory elements like promoters, enhancers, switch regions, recombination signals, and the like may be of human or non-human origin. What is required is that the elements be operable in the animal species concerned, in order to render the artificial loci functional.

In one aspect, the invention provides transgenic constructs containing an artificial heavy chain locus capable of undergoing gene rearrangement in the host animal thereby producing a diversified repertoire of heavy chains having human idiotypes. An artificial heavy chain locus of the transgene contains a V-region with at least one human V gene segment. Preferably, the V-region includes at least about 5-100 human heavy chain V (or "VH") gene segments. As described above, a human VH segment encompasses naturally occurring sequences of a human VH gene segment, degenerate forms of naturally occurring sequences of a human VH gene segment, as well as synthetic sequences that encode a polypeptide sequence substantially (i.e., at least about 85%-95%) identical to a human heavy chain V domain polypeptide.

In a preferred embodiment, the artificial heavy chain locus contains at least one or several rat constant region genes, e.g., Cδ, Cμ and Cγ (including any of the Cγ subclasses).

In another preferred embodiment, the artificial heavy chain locus contains artificial constant region genes. In a preferred embodiment, such artificial constant region genes encode a human CH1 domain and rat CH2 CH3 domains, or a human CH1 and rat CH2, CH3 and CH4 domains. A hybrid heavy chain with a human CH1 domain pairs effectively with a fully human light chain.

In another preferred embodiment, the artificial heavy chain locus contains artificial constant region genes lacking CH1 domains In a preferred embodiment, such artificial constant region genes encode truncated IgM and/or IgG lacking the CH1 domain but comprising CH2, and CH3, or CH1, CH2, CH3 and CH4 domains. Heavy chains lacking CH1 domains cannot pair effectively with Ig light chains and form heavy chain only antibodies.

In another aspect, the invention provides transgenic constructs containing an artificial light chain locus capable of undergoing gene rearrangement in the host animal thereby producing a diversified repertoire of light chains having human idiotypes. An artificial light chain locus of the transgene contains a V-region with at least one human V gene segment, e.g., a V-region having at least one human VL gene and/or at least one rearranged human VJ segment. Preferably, the V-region includes at least about 5-100 human light chain V (or "VL") gene segments. Consistently, a human VL segment encompasses naturally occurring sequences of a human VL gene segment, degenerate forms of naturally occurring sequences of a human VL gene segment, as well as synthetic sequences that encode a polypeptide sequence substantially (i.e., at least about 85%-95%) identical to a human light chain V domain polypeptide. In one embodiment, the artificial light chain Ig locus has a C-region having at least one rat C gene (e.g., rat Cλ or Cκ.

Another aspect of the present invention is directed to methods of making a transgenic vector containing an artificial Ig locus. Such methods involve isolating Ig loci or fragments thereof, and combining the same, with one or several DNA fragments comprising sequences encoding human V region elements. The Ig gene segment(s) are inserted into the artificial Ig locus or a portion thereof by ligation or homologous recombination in such a way as to retain the capacity of the locus to undergo effective gene rearrangement in the subject animal.

Preferably, a non-human Ig locus is isolated by screening a library of plasmids, cosmids, YACs or BACs, and the like, prepared from the genomic DNA of the same. YAC clones can carry DNA fragments of up to 2 megabases, thus an entire animal heavy chain locus or a large portion thereof can be isolated in one YAC clone, or reconstructed to be contained in one YAC clone. BAC clones are capable of carrying DNA fragments of smaller sizes (about 50-500 kb). However, multiple BAC clones containing overlapping fragments of an Ig locus can be separately altered and subsequently injected together into an animal recipient cell, wherein the overlapping fragments recombine in the recipient animal cell to generate a continuous Ig locus.

Human Ig gene segments can be integrated into the Ig locus on a vector (e.g., a BAC clone) by a variety of methods, including ligation of DNA fragments, or insertion of DNA fragments by homologous recombination. Integration of the human Ig gene segments is done in such a way that the human Ig gene segment is operably linked to the host animal sequence in the transgene to produce a functional humanized Ig locus, i.e., an Ig locus capable of gene rearrangement which lead to the production of a diversified repertoire of antibodies with human idiotypes. Homologous recombination can be performed in bacteria, yeast and other cells with a high frequency of homologous recombination events. Engineered YACs and BACs can be readily isolated from the cells and used in making transgenic animals.

Immunoglobulins Having a Human Idiotype

Once a transgenic animal capable of producing immunoglobulins having a human idiotype is made, immunoglobulins and antibody preparations against an antigen can be readily obtained by immunizing the animal with the antigen. "Polyclonal antisera composition" as used herein includes affinity purified polyclonal antibody preparations.

A variety of antigens can be used to immunize a transgenic animal. Such antigens include but are not limited to, microorganisms, e.g. viruses and unicellular organisms (such as bacteria and fungi), alive, attenuated or dead, fragments of the microorganisms, or antigenic molecules isolated from the microorganisms.

Preferred bacterial antigens for use in immunizing an animal include purified antigens from *Staphylococcus aureus* such as capsular polysaccharides type 5 and 8, recombinant versions of virulence factors such as alpha-toxin, adhesin binding proteins, collagen binding proteins, and fibronectin binding proteins. Preferred bacterial antigens also include an attenuated version of *S. aureus, Pseudomonas aeruginosa, enterococcus, enterobacter*, and *Klebsiella pneumoniae*, or culture supernatant from these bacteria cells. Other bacterial antigens which can be used in immunization include purified lipopolysaccharide (LPS), capsular antigens, capsular polysaccharides and/or recombinant versions of the outer membrane proteins, fibronectin binding proteins, endotoxin, and exotoxin from *Pseudomonas aeruginosa, enterococcus, enterobacter*, and *Klebsiella pneumoniae*.

Preferred antigens for the generation of antibodies against fungi include attenuated version of fungi or outer membrane proteins thereof, which fungi include, but are not limited to, *Candida albicans, Candida parapsilosis, Candida tropicalis*, and *Cryptococcus neoformans*.

Preferred antigens for use in immunization in order to generate antibodies against viruses include the envelop proteins and attenuated versions of viruses which include, but are not limited to respiratory synctial virus (RSV) (particularly the F-Protein), Hepatitis C virus (HCV), Hepatitis B virus (HBV), cytomegalovirus (CMV), EBV, and HSV.

Antibodies specific for cancer can be generated by immunizing transgenic animals with isolated tumor cells or tumor cell lines as well as tumor-associated antigens which include, but are not limited to, Her-2-neu antigen (antibodies against which are useful for the treatment of breast cancer); CD20, CD22 and CD53 antigens (antibodies against which are useful for the treatment of B cell lymphomas), prostate specific membrane antigen (PMSA) (antibodies against which are useful for the treatment of prostate cancer), and 17-1A molecule (antibodies against which are useful for the treatment of colon cancer).

The antigens can be administered to a transgenic animal in any convenient manner, with or without an adjuvant, and can be administered in accordance with a predetermined schedule.

For making a monoclonal antibody, spleen cells are isolated from the immunized transgenic animal and used either in cell fusion with transformed cell lines for the production of hybridomas, or cDNAs encoding antibodies are cloned by standard molecular biology techniques and expressed in transfected cells. The procedures for making monoclonal antibodies are well established in the art. See, e.g., European Patent Application 0 583 980 A1 ("Method For Generating Monoclonal Antibodies From Rabbits"), U.S. Pat. No. 4,977,081 ("Stable Rabbit-Mouse Hybridomas And Secretion Products Thereof"), WO 97/16537 ("Stable Chicken B-cell Line And Method of Use Thereof"), and EP 0 491 057 B1 ("Hybridoma Which Produces Avian Specific Immunoglobulin G"), the disclosures of which are incorporated herein by reference. In vitro production of monoclonal antibodies from cloned cDNA molecules has been described by Andris-Widhopf et al., "Methods for the generation of chicken monoclonal antibody fragments by phage display", *J Immunol Methods* 242:159 (2000), and by Burton, D. R., "Phage display", *Immunotechnology* 1:87 (1995).

Once chimeric monoclonal antibodies with human idiotypes have been generated, such chimeric antibodies can be easily converted into fully human antibodies using standard molecular biology techniques. Fully human monoclonal antibodies are not immunogenic in humans and are appropriate for use in the therapeutic treatment of human subjects.

Antibodies of the Invention Include Heavy Chain-Only Antibodies

In one embodiment, transgenic animals which lack a functional Ig light chain locus, and comprising an artificial heavy chain locus, are immunized with antigen to produce heavy chain-only antibodies that specifically bind to antigen.

In one embodiment, the invention provides monoclonal antibody producing cells derived from such animals, as well as nucleic acids derived therefrom. Also provided are hybridomas derived therefrom. Also provided are fully human heavy chain-only antibodies, as well as encoding nucleic acids, derived therefrom.

Teachings on heavy chain-only antibodies are found in the art. For example, see PCT publications WO02085944, WO02085945, WO2006008548, and WO2007096779. See also U.S. Pat. No. 5,840,526; U.S. Pat. No. 5,874,541; U.S. Pat. No. 6,005,079; U.S. Pat. No. 6,765,087; U.S. Pat. No. 5,800,988; EP 1589107; WO 9734103; and U.S. Pat. No. 6,015,695.

Pharmaceutical Compositions

In a further embodiment of the present invention, purified monoclonal or polyclonal antibodies are admixed with an appropriate pharmaceutical carrier suitable for administration to patients, to provide pharmaceutical compositions.

Patients treated with the pharmaceutical compositions of the invention are preferably mammals, more preferably humans, though veterinary uses are also contemplated.

Pharmaceutically acceptable carriers which can be employed in the present pharmaceutical compositions can be any and all solvents, dispersion media, isotonic agents and the like. Except insofar as any conventional media, agent, diluent or carrier is detrimental to the recipient or to the therapeutic effectiveness of the antibodies contained therein, its use in the pharmaceutical compositions of the present invention is appropriate.

The carrier can be liquid, semi-solid, e.g. pastes, or solid carriers. Examples of carriers include oils, water, saline solutions, alcohol, sugar, gel, lipids, liposomes, resins, porous matrices, binders, fillers, coatings, preservatives and the like, or combinations thereof.

Methods of Treatment

In a further aspect of the present invention, methods are provided for treating a disease in a vertebrate, preferably a mammal, preferably a primate, with human subjects being an especially preferred embodiment, by administering a purified antibody composition of the invention desirable for treating such disease.

The antibody compositions can be used to bind and neutralize or modulate an antigenic entity in human body tissues that causes or contributes to disease or that elicits undesired or abnormal immune responses. An "antigenic entity" is herein defined to encompass any soluble or cell surface bound molecules including proteins, as well as cells or infectious disease-causing organisms or agents that are at least capable of binding to an antibody and preferably are also capable of stimulating an immune response.

Administration of an antibody composition against an infectious agent as a monotherapy or in combination with chemotherapy results in elimination of infectious particles. A single administration of antibodies decreases the number of infectious particles generally 10 to 100 fold, more commonly more than 1000-fold. Similarly, antibody therapy in patients with a malignant disease employed as a monotherapy or in combination with chemotherapy reduces the number of malignant cells generally 10 to 100 fold, or more than 1000-fold. Therapy may be repeated over an extended amount of time to assure the complete elimination of infectious particles, malignant cells, etc. In some instances, therapy with antibody preparations will be continued for extended periods of time in the absence of detectable amounts of infectious particles or undesirable cells.

Similarly, the use of antibody therapy for the modulation of immune responses may consist of single or multiple administrations of therapeutic antibodies. Therapy may be continued for extended periods of time in the absence of any disease symptoms.

The subject treatment may be employed in conjunction with chemotherapy at dosages sufficient to inhibit infectious disease or malignancies. In autoimmune disease patients or transplant recipients, antibody therapy may be employed in conjunction with immunosuppressive therapy at dosages sufficient to inhibit immune reactions.

All citations are expressly incorporated herein in their entirety by reference.

EXPERIMENTAL

Directed Evolution of Homing Endonucleases Specific for Rat Immunoglobulin Sequences.

An analysis of rat IgM exon sequences resulted in the identification of several target cleavage sequences for engineered homing endonucleases. Using homing endonuclease I-ScelI, two target sequences were identified, one within rat IgM exon II (CGTGGATCACAGGGGTCT) (SEQ. I.D. NO. 1), and the other within rat IgM exon III (CTGGGATAA-CAGGAAGGA) (SEQ. I.D. NO. 2). These sites share 61% (11 out of 18 bases) sequence identity with the natural recognition sequence of I-ScelI (TAGGGATAACAGGGTAAT) (SEQ. I.D. NO. 3).

TABLE 1

Target sequences in rat IgM exons (the different nucleotides are underlined)

| Target | Sequence | Similarity | position |
|---|---|---|---|
| T3 | CGTGGATCACAGGGGTCT (SEQ. I.D. NO. 1) | 61% | Exon II |
| T4 | CTGGGATAACAGGAAGGA (SEQ. I.D. NO. 2) | 61% | Exon III |
| Wild Type | TAGGGATAACAGGGTAAT (SEQ. I.D. NO. 3) | | |

For the engineering of homing endonucleases specific for these target sequences we used a highly sensitive selection for the directed evolution of homing endonucleases that couples enzymatic DNA cleavage with the survival of host cells (described in detail by Chen and Zhao, Nucleic Acids Research 33(18):e154, 2005). An in vitro coevolution strategy was used to engineer I-ScelI variants with target sequence specificity. As shown in Table 2, for target sequence T3, two new sequences, T3i1 and T3i2, were selected as intermediate sequences, while for target sequence T4, two new sequences, T4i1 and T4i2, were selected as intermediate sequences. The T3i1 and T4i1 sequences were cloned into the report plasmid to yield p11-LacY-T3i1 and p11-LacY-T4 i1, respectively.

TABLE 2

Sequences in three steps (the different nucleotides are underlined)

| | | |
|---|---|---|
| Step T3i1 1 | TAGGGATAACAGGG<u>GTCT</u><br>SEQ. I.D. NO. 4 | TAGGGATAACAGGG<u>AGGA</u><br>SEQ. I.D. NO. 6 |
| Step T3i2 2 | <u>CG</u>TGGATAACAGGG<u>GTCT</u><br>SEQ. I.D. NO. 5 | <u>CT</u>GGGATAACAGGA<u>AGGA</u><br>SEQ. I.D. NO. 2 |
| Step T3 3 | <u>CGT</u>GGAT<u>C</u>ACAGGG<u>GTCT</u><br>SEQ. I.D. NO. 1 | <u>CT</u>GGGATAACAGG<u>AAGGA</u><br>SEQ. I.D. NO. 2 |

Figure 2:
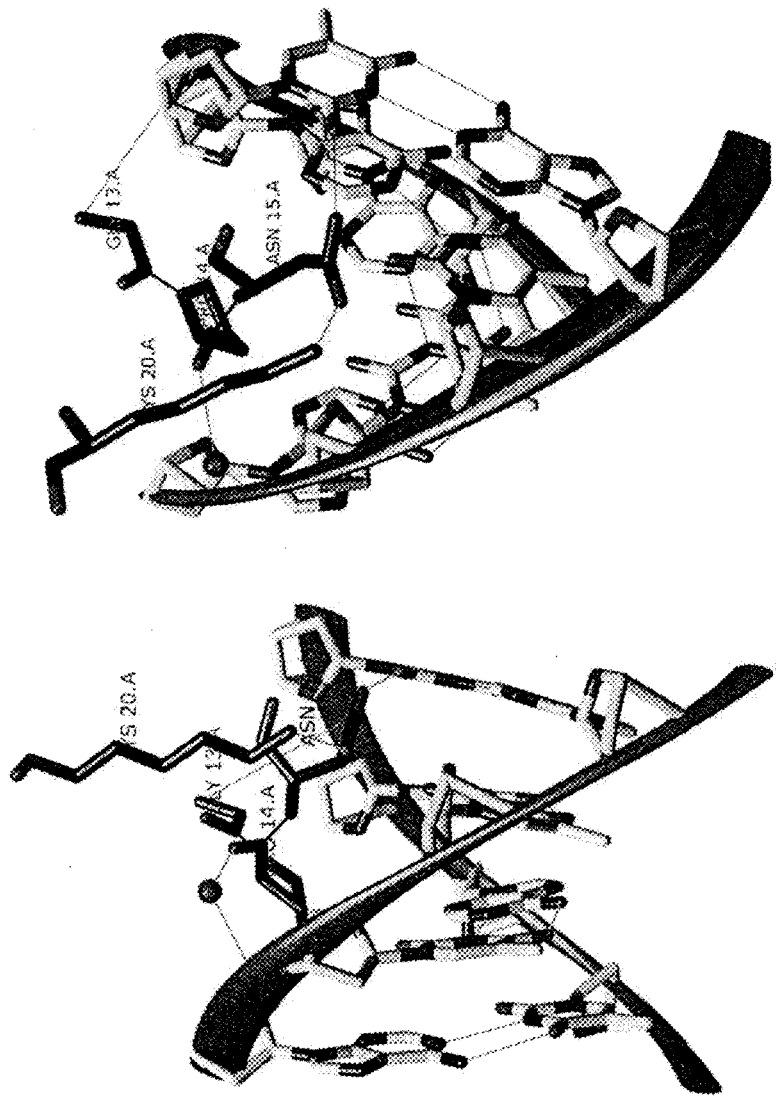
FIG. 2. Schematic of the interaction of I-SceI and DNA at 3' end of recognition sequence.
Figure 3:
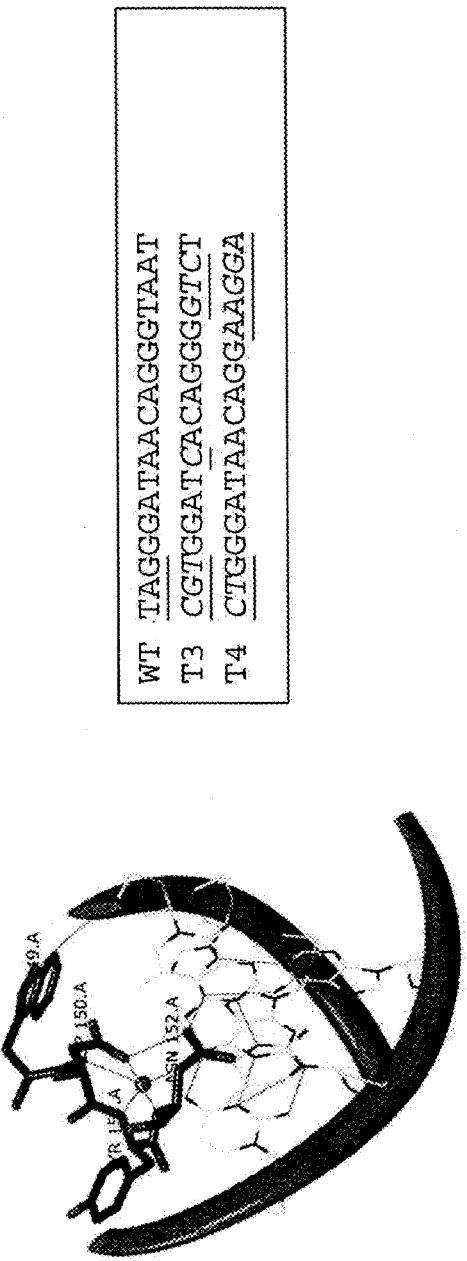
FIG. 3. Schematic of the interaction of the 5' end of the I-SceI recognition sequence with I-SceI, wherein WT is SEQ. I.D. NO. 3; T3 is SEQ. I.D. NO. 1; and T4 is SEQ. I.D. NO. 2.

To obtain I-SceI mutants with T3i1 or T4i1 sequence specificity, molecular modeling was first carried out to identify the residues to be used to create a focused library via saturation mutagenesis. As shown in FIG. 2, I-SceI binds to the 3' end of T3i1 or T4i1 through a relaxed loop that lies in the minor groove of DNA. Residues Gly13, Pro14, Asn15 and Lys20 are close to this 3' end and Asn15 binds directly to the last thymine at the 3' end of the wild type recognition sequence through hydrogen bonds. A library of mutants containing all the possible combinations of amino acid substitutions at these four select residues were constructed by saturation mutagenesis. To generate a large enough library, the ligation reaction and DNA transformation procedures were optimized through several trials. A library consisting of 2.9 10$^6$ mutants was created.

The library was screened for I-SceI mutants with increased activity towards the T3i1 sequence. Compared to round 0 (wild type I-SceI), the first round of screening yielded mutants with increased activity toward the T3i1 sequence since the cell survival rate was increased by 10-fold. Enrichment of the potentially positive mutants in round 2 and 3 showed further improvement in cell survival rate. Similarly, the library was screened for I-SceI mutants with increased activity towards the T4i1 sequence. Screening of mutants yielded mutants with increased activity toward the T4i1 sequence.

In parallel, a second library of I-SceI mutants targeting the 5' end of the recognition sequence was designed. The first library created using saturation mutagenesis was focused on those residues interacting with the 3' end of the four nucleotides of the I-SceI recognition sequence. Based on molecular modeling, Trp149, Asp150, Tyr151 and Asn152 lie in the major groove formed by the 5' end nucleotides. Asn152 interacts directly with T(−7) though hydrogen bonding. Asp150 and Tyr152 interact T opposite to A(−6) indirectly though a water molecule. Trp149 and Tyr151 interact with the phosphate backbone. Thus these four residues are important to the sequence specificity of I-SceI and simultaneous saturation mutagenesis on these four residues was done to create a second I-SceI mutant library.

Further coevolution of these enzymes results in the generation of novel meganucleases specific for target sequences in rat IgM exons II and III (CGTGGATCACAGGGGTCT (SEQ. I.D. NO. 1) and CTGGGATAACAGGAAGGA (SEQ. I.D. NO. 2)).

Engineering of I-CreI with Defined Sequence Specificity

Figure 4:
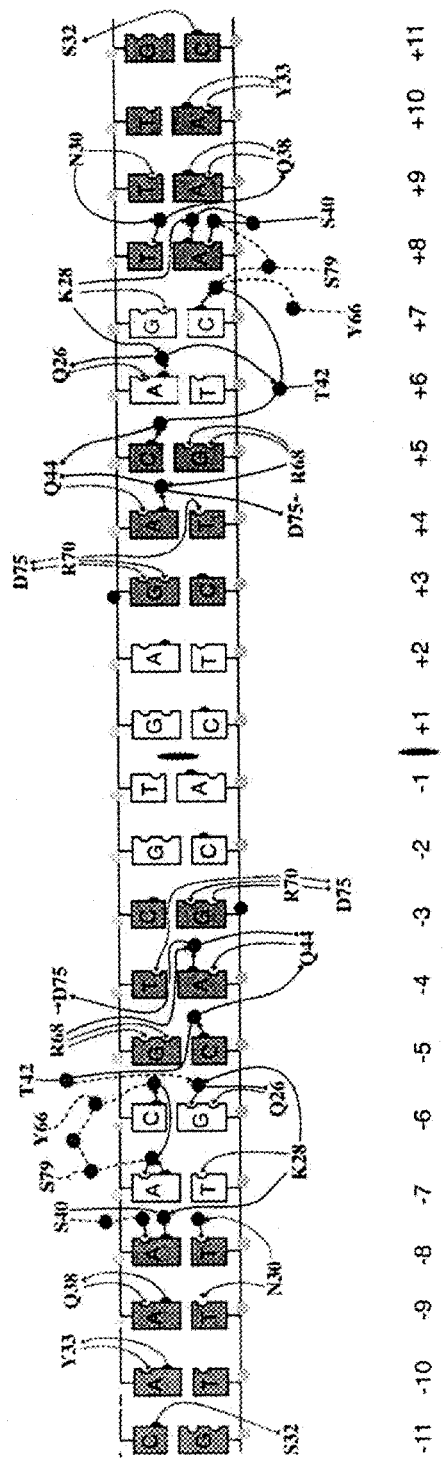
FIG. 4. Schematic of sequence recognition mechanism of I-CreI (from Nucleic Acids Res., 34, 4791-4800), wherein the first sequence is SEQ. ID. NO. 8 and the second sequence is SEQ. ID. NO. 58.
Figure 5:
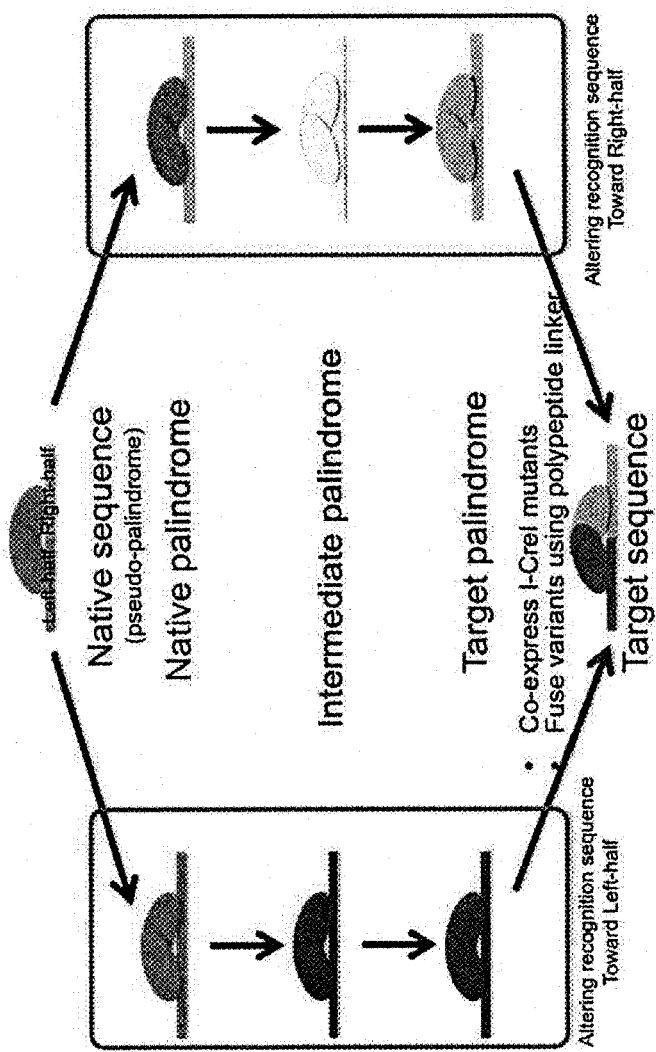
FIG. 5. Schematic diagram of the strategy for altering recognition sequence of I-CreI.

For the engineering of homing endonucleases specific for novel target sequences we used a highly sensitive selection for the directed evolution of homing endonucleases that couples enzymatic DNA cleavage with the survival of host cells (described in detail by Chen and Zhao, Nucleic Acid Research 33(18):e154, 2005). In addition, a general strategy for engineering I-CreI mutant with defined sequence specificity was designed. I-CreI recognizes a target sequence in a pseudo palindromic manner. Palindromic bases are directly recognized by I-CreI and may be difficult to be altered (*J. Mol. Biol.*, 280, 345-353) (FIG. 4).

This property hinders the direct engineering of I-CreI derivatives that recognize a non-palindromic sequence. To overcome this problem, the target sequence was divided into left-half (upstream-half) and right-half (downstream-half). I-CreI is optimized for the intermediate sequences of the left-half palindrome and the right-half palindrome, respectively (FIG. 4). Then, the I-CreI mutants, optimized for intermediate sequences, are engineered to recognize the target sequence palindrome. Finally, I-CreI mutant respectively optimized for left-half and that for right-half will be co-expressed to cleave the target sequence. In addition, fusion of the left-half optimized mutant with the right-half optimized mutant by a polypeptide linker is examined.

A target sequence within exon IV (CAACTGATCCT-GAGGGAGTCGG) (SEQ. I.D. NO. 7) that shares 59% sequence identity with the natural recognition sequence of homing endonuclease I-CreI was identified. Subsequently, based on the identity of palindromic bases within the original I-CreI target sequence, two sequences, T5 and T6, were selected as target sequences for I-CreI engineering.

| | −11 | −10 | −9 | −8 | −7 | −6 | −5 | −4 | −3 | −2 | −1 | 1 | 2 | 3 | 4 | 5 | 6 | 7 | 8 | 9 | 10 | 11 | Homology | |
|---|---|---|---|---|---|---|---|---|---|---|---|---|---|---|---|---|---|---|---|---|---|---|---|---|
| | First half | | | | | | | | | | | Second half | | | | | | | | | | | | |
| Original *SID 8 | C | A | A | A | A | C | C | T | C | C | G | T | G | A | G | A | C | A | G | T | T | T | G | Total Palindromic |
| T5 *SID 9 | A | A | A | A | A | T | G | T | C | C | T | T | G | A | A | G | G | T | T | C | A | G | 50.0% | 64.3% |
| T6 *SID 7 | C | A | A | C | T | G | A | T | C | C | T | G | A | G | G | G | A | G | T | C | G | G | 59.1% | 57.1% |

Palindromic bases are highlighted. Conserved bases are written in bold face.

(*SID refers to SEQ. I.D. NO.)

The two target sequences, T5 and T6, were cloned into reporter plasmids. The I-CreI gene was cloned into the pTrc plasmid and sequenced to confirm that no mutations were introduced during PCR amplification. The I-CreI selection system is evaluated for cell survival rates.

In addition, molecular modeling was performed and protein residues that contact directly the DNA substrate were identified. In addition, we designed the intermediate sequences for in vitro co-evolution experiments.

Target Residues for Saturation Mutagenesis

| | Target residue |
|---|---|
| YN-TS5-L | Q26 and S32 |
| YN-TS5-Ri1 | R68, R70 and D75 |
| YN-TS5-Ri2 | Q26 and K28 |
| YN-TS5-Ri3 | N30, Y33 and Q38 |
| YN-TS6-L | Q26, K28 and R68 |
| YN-TS6-Ri1 | Q44 and R68 |
| YN-TS6-Ri2 | N30, Y33 and Q38 |

Subsequently, libraries of ICreI mutants are generated and screened for ICreI derivatives with novel target sequences. Further coevolution of these enzymes results in the generation of novel meganucleases specific for a target sequence within exon IV of rat IgM (CAACTGATCCTGAGG-GAGTCGG) (SEQ. I.D. NO 7).

Engineering of Zinc-Finger Nucleases

Figure 6:
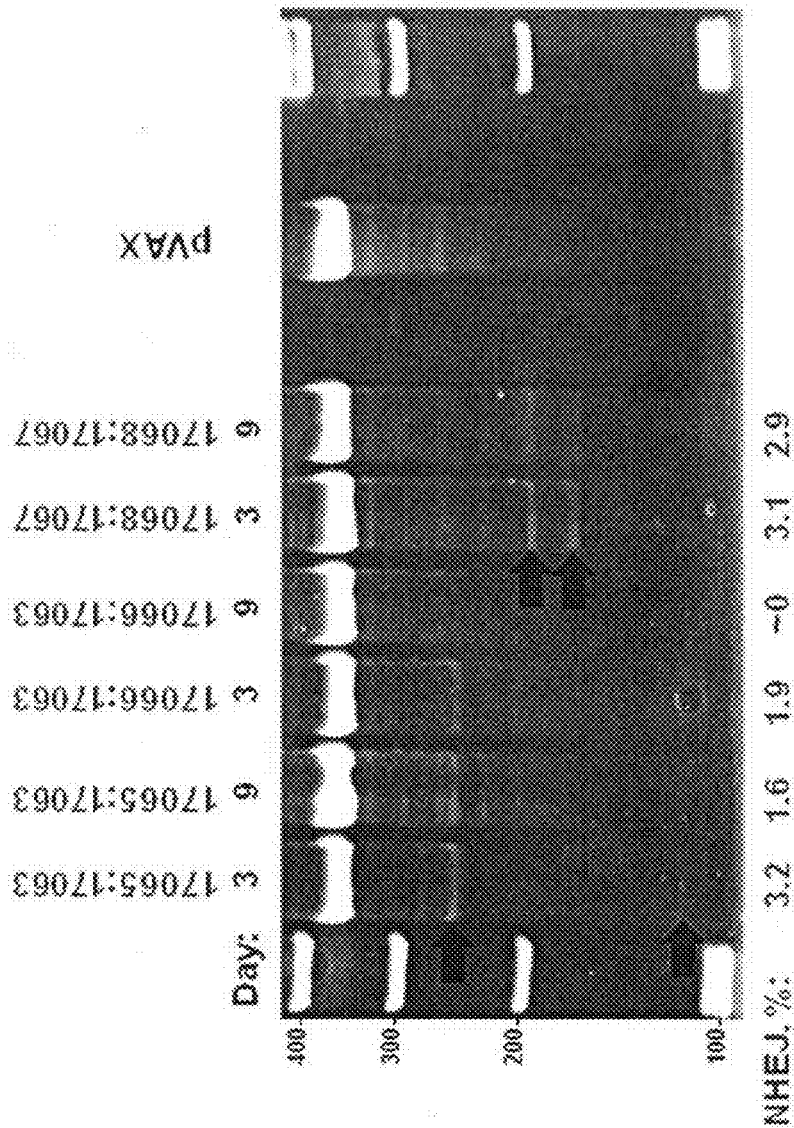
FIG. 6. Zinc-finger proteins (ZFP) designed against sequences encoding rat IgM were expressed in cells, chromosomal DNA was prepared, and the appropriate region of the IgM locus was PCR amplified. Reaction products were analyzed by polyacrylamide gel electrophoresis. The figure shows a typical example demonstrating cleavage activity.

Zinc-finger proteins (ZFP) were designed against sequences encoding rat IgM (exons 1-4) and assembled as described (Zhang, L. et al. Synthetic zing finger transcription factor action at an endogenous chromosomal site. Activation of the human erythropoietin gene. J. Biol. Chem 275:33850-33860, 2000, and Liu, P. Q. et al. Regulation of an endogenous locus against a panel of designed zinc finger proteins targeted to accessible chromatin regions. Activation of vascular endothelial growth factor. J Biol. Chem. 2765:11323-11334, 2001), to yield the following ZFP moieties DNA polymerase (Invitrogen). PCR reactions were heated to 94°, then gradually cooled to room temperature. Approximately 200 ng of the annealed DNA was mixed with 0.33 µL CEL-I enzyme (Transgenomic) and incubated for 20 minutes at 42°. Reaction products were analyzed by polyacrylamide gel electrophoresis in 1× Tris-borate-EDTA buffer. A typical example demonstrating cleavage activity is shown in FIG. 6.

Generation of Rats with Inactivated Endogenous Heavy Chain Locus Using Expression Plasmids Encoding a Meganuclease A cDNA sequence encoding a meganuclease specific for a rat Cµ exon is cloned into an expression vector where expression is controlled by the tetracycline operator sequence. Plasmid DNA is linearized by restriction enzyme digestion and purified. Rat oocytes are fertilized with sperm form rats with a transgene encoding a tetracycline-responsive reverse transactivator. Purified plasmid DNA is injected into pronuclei of such fertilized rat oocytes. Subsequently, rat embryos are transferred into foster mothers and brought to term. Newborns are analyzed for the presence of meganuclease-encoding transgene by PCR using DNA isolated from tissue samples. Male transgenic founder animals are housed for four months when they reach sexual maturity. Expression of meganuclease in transgenic animals is induced by daily administration of doxycycline for one to seven days. Subsequently, sperm is collected twice per week and analyzed by PCR. Male animals producing mutated sperm are used for

| SBS | Recognition sequence | Finger 1 | Finger 2 | Finger 3 | Finger 4 | Finger 5 | Finger 6 | Linker 2-3 | Linker 4-5 |
|---|---|---|---|---|---|---|---|---|---|
| 17063 | AGACAGGGGGCTCTC | NKVGLIE SID 10 | TSSDLSR SID 11 | RSDHLSR SID 12 | RSDNLSE SID 13 | QNAHRKT SID 14 | | TGGERP SID 15 | TGEKP SID 16 |
| 17065 | AATTTGGTGGCCATG | RSDALST SID 18 | DRSTRTK SID 19 | RSDALAR SID 20 | RSDSLSA SID 21 | TSSNRKT SID 22 | | TGGQRP SID 23 | TGEKP SID 17 |
| 17067 | GTTCTGGTAGTT | RSANLAR SID 25 | RSDNLRE SID 26 | TSGSLSR SID 27 | QSGSLTR SID 28 | RSDVLSE SID 29 | | TGGGGSQRP SID 30 | TGSQKP SID 31 |
| 17068 | GAAGTCATGCAGGGTGTC | DRSALSR SID 32 | TSGHLSR SID 33 | RSDNLST SID 34 | HNATRIN SID 35 | DRSALSR SID 36 | TSGSLTR SID 37 | TGGQRP SID 34 | TGSQKP SID 38 |
| 17089 | GGTGCCATTGGGGTG | RSDALAR SID 39 | RSDHLST SID 21 | HSNARKN SID 40 | ERGTLAR SID 41 | TSGHLSR SID 42 | QSGNLAR SID 35 | TGEKP SID 43 | TGSQKP SID 17 |
| 17090 | GCTGTGGGTGTGGCT | QSSDLSR SID 44 | RSDALTQ SID 45 | TSGHLSR SID 46 | RSDALSR SID 35 | DRSDLSR SID 47 | | TGGQRP SID 48 | TGEKP SID 25 |
| 17119 | ACCATGTGTGGCAGGG | RSAHLSR SID 49 | QSGDLTR SID 50 | RSDALAR SID 51 | RSDTLSV SID 21 | DNSTRIK SID 52 | | TGEKP SID 53 | TGEKP SID 17 |
| 17120 | GAGGACCGTGGACAAG | RSANLSV SID 54 | DRANLSR SID 55 | RSDALAR SID 56 | DRSDLSR SID 21 | RSDDLTR SID 48 | | TGEKP SID 57 | TGEKP SID 17 |

(*SID represents SEQ. I.D. NO.)

DNA encoding ZFPs were cloned into an expression vector. Rat C6 cells were obtained from the American Type Culture Collection and grown as recommended in F-12 medium (Invitrogen) supplemented with 5% qualified fetal calf serum (FCS, Hyclone), 15% horse serum (Invitrogen) and 5 mM glutamine. Cells were disassociated from plasticware using TrypLE Select protease (Invitrogen). For transfection, 200,000 C6 cells were mixed with 400 ng plasmid DNA and 20 µL Amaxa Solution SF. Cells were transfected in an Amaxa Nucleofector II Shuttle using program 96 FF-137 and recovered into 0.1 L warm, supplemented, F-12 medium. Three and nine days post transfection cells were harvested and chromosomal DNA was prepared using a Quick Extract Solution 1.0 (Epicentre). The appropriate region of the IgM locus was PCR amplified using Accuprime High-fidelity breeding. Offspring with mutated rat Cµ are identified by PCR analysis of tissue samples.

Generation of Rats with Inactivated Endogenous Heavy Chain Locus by Microinjection of Fertilized Oocytes with Plasmid DNA Encoding a Specific Meganuclease A cDNA sequence encoding a meganuclease specific for a rat Cµ exon is cloned into an expression vector where expression is controlled by the CAG-promoter. Purified plasmid DNA is is injected into pronuclei of fertilized rat oocytes. Subsequently, rat embryos are transferred into foster mothers and brought to term. Newborns are analyzed for the presence mutated IgM exons by PCR and direct sequencing. Alternatively, animals containing cells with mutated IgM exons are identified by incubation of heated and cooled PCR products with CEL-I enzyme and subsequent gel electrophoresis.

I claim:

1. A transgenic rat whose genome comprises a functionally ablated endogenous immunoglobulin (Ig) heavy chain gene and/or a functionally ablated endogenous Ig light chain gene.

2. The transgenic rat according to claim 1 whose genome further comprises a nucleic acid sequence encoding an exogenous human Ig gene capable of producing immunoglobulins with human idiotypes.

3. The transgenic rat according to claim 2, wherein the exogenous human Ig gene is an Ig light chain gene and/or an Ig heavy chain gene.

4. The transgenic rat according to claim 2, wherein the exogenous human Ig gene comprises human immunoglobulin gene segments and rat immunoglobulin gene segments, wherein the human immunoglobulin gene segments comprise: (i) at least one human variable (V) gene segment and/or (ii) at least one human diverse (D) gene segment.

5. The transgenic rat according to claim 4, wherein the human immunoglobulin gene segments comprise a nucleic acid sequence selected from the group consisting of: i) naturally occurring human Ig gene sequences; ii) degenerate forms of naturally occurring human Ig gene sequences; and iii) synthetic sequences encoding a polypeptide sequence that is 85%-95% identical to the polypeptide encoded by a naturally occurring human Ig gene sequence.

* * * * *